(12) United States Patent
Zenker et al.

(10) Patent No.: US 6,245,051 B1
(45) Date of Patent: Jun. 12, 2001

(54) ABSORBENT ARTICLE WITH A LIQUID DISTRIBUTION, BELT COMPONENT

(75) Inventors: David Louis Zenker, Neenah; Hoa La Wilhelm; Rob David Everett, both of Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/243,914

(22) Filed: Feb. 3, 1999

(51) Int. Cl.⁷ ........................................................ A61F 13/15
(52) U.S. Cl. ............................................................. 604/385.23
(58) Field of Search ................ 604/378, 385.21–385.29, 604/385.3, 389, 368, 358, 372

(56) References Cited

U.S. PATENT DOCUMENTS

| | | |
|---|---|---|
| 3,901,236 | 8/1975 | Assarsson et al. . |
| 4,076,663 | 2/1978 | Masuda et al. . |
| 4,286,082 | 8/1981 | Tsubakimoto et al. . |
| 4,663,220 | 5/1987 | Wisneski et al. . |
| 4,699,823 | 10/1987 | Kellenberger et al. . |
| 4,704,116 | 11/1987 | Enloe . |
| 4,753,646 | 6/1988 | Enloe . |
| 4,916,005 | 4/1990 | Lippert et al. . |
| 4,938,753 | 7/1990 | Van Gompel et al. . |
| 5,019,073 | 5/1991 | Roessler et al. . |
| 5,226,992 | 7/1993 | Morman . |
| 5,399,219 | 3/1995 | Roessler et al. . |
| 5,486,166 | 1/1996 | Bishop et al. . |
| 5,490,846 | 2/1996 | Ellis et al. . |
| 5,540,796 | 7/1996 | Fries . |
| 5,562,650 | 10/1996 | Everett et al. . |
| 5,595,618 | 1/1997 | Fries et al. . |
| 5,605,735 | 2/1997 | Zehner et al. . |
| 5,624,429 | 4/1997 | Long et al. . |
| 5,629,377 | 5/1997 | Burgert et al. . |
| 5,820,973 | 10/1998 | Dodge, II et al. . |
| 5,843,063 | 12/1998 | Anderson et al. . |
| 5,843,852 | 12/1998 | Dutkiewicz et al. . |
| 5,858,515 | 1/1999 | Stokes et al. . |
| 5,904,675 | 5/1999 | Laux et al. . |

FOREIGN PATENT DOCUMENTS

| | | |
|---|---|---|
| 0 217 032 A2 | 4/1987 | (EP) . |
| WO 95/16425 A2 | 6/1995 | (WO) . |
| WO 96/09435 A1 | 3/1996 | (WO) . |
| WO 96/32084 A1 | 10/1996 | (WO) . |

OTHER PUBLICATIONS

Federal Test Method Standard (FTMS) No. 191A, Method 5514, "Water Resistance of Cloth; Low Range, Hydrostatic Pressure Method," Jul. 20, 1978, 3 pages.

TAPPI Official Test Method T 543 om–94, "Bending Resistance of Paper (Gurley Type Tester)," published by the TAPPI Press, Atlanta, Georgia, pp. 1–7.

Primary Examiner—Anhtuan T. Nguyen
(74) Attorney, Agent, or Firm—Paul Yee

(57) ABSTRACT

An absorbent article (10) has a longitudinal direction (26), a lateral direction (24), a first waistband portion (12), a second waistband portion (14) and an intermediate portion (16) interconnecting the first and second waistband portions. The article (10) includes a backsheet layer (30); a liquid permeable top sheet layer (28); and an absorbent structure (32) sandwiched between the backsheet and topsheet layers. The absorbent structure includes a retention portion (48) having a first retention section (47) and a longitudinally opposed second retention section (49). A liquid distribution, waist belt component (52) has a belt first end region (54), a belt second end region (56) and a belt medial region (58) interconnecting the belt first and second end regions. The belt first end region (54) is joined to the article in liquid communication with the first retention section (47), and the distribution belt component (52) has sufficient lateral length to extend along a wearer's waist area to position the belt second end region (56) in liquid communication with the second retention section (49) when the article is worn.

27 Claims, 17 Drawing Sheets

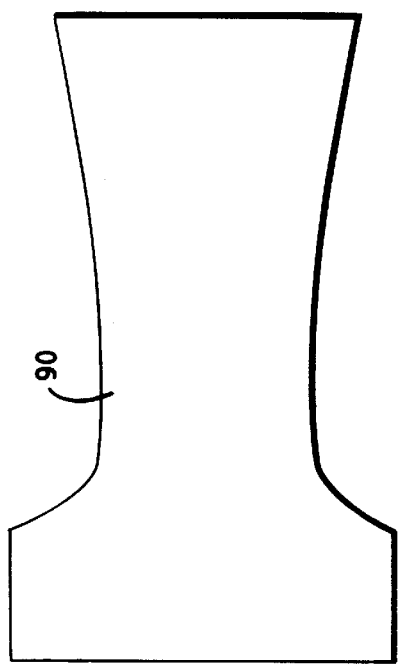
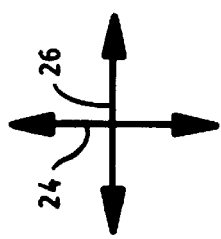
FIG. 5
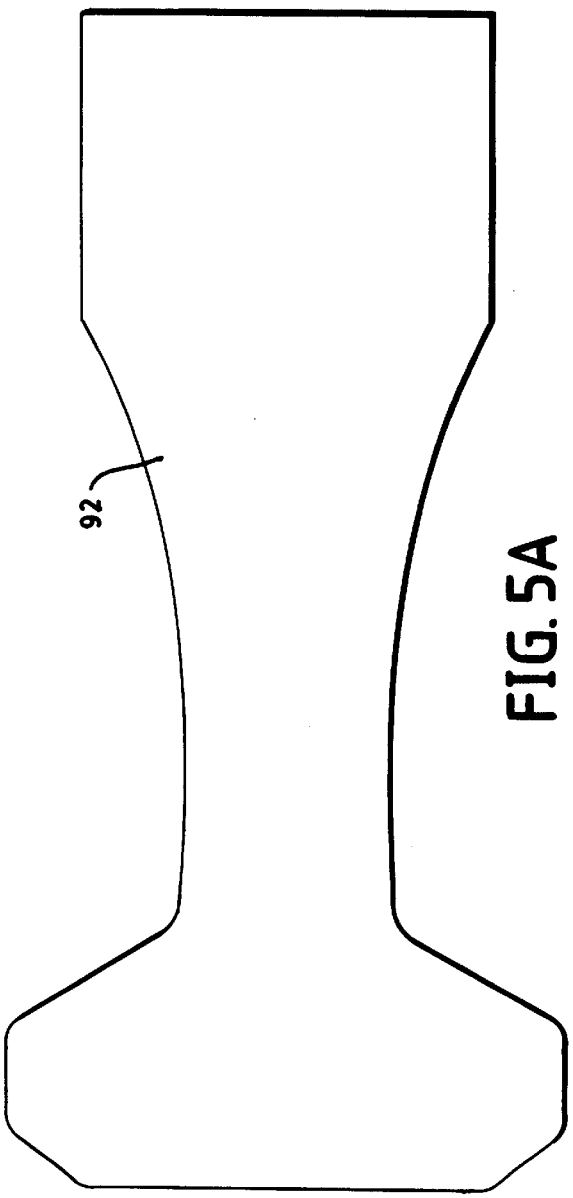
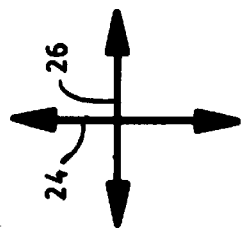
FIG. 5A

ABSORBENT ARTICLE WITH A LIQUID DISTRIBUTION, BELT COMPONENT

FIELD OF THE INVENTION

The present invention relates to absorbent articles. More particularly, the present invention relates to an absorbent article having a distinctive liquid-distribution member which more effectively transports liquids for more efficient retention and storage.

BACKGROUND OF THE INVENTION

The performance objectives of disposable absorbent articles, such as infant diapers, include leakage prevention, dry feel to the wearer, and a comfortable fit throughout the product life. Accordingly, absorbent articles have typically contained an absorbent core to provide liquid handling and other absorbent functionalities required to meet the product performance objectives. The absorbent core of a conventional absorbent article has typically been composed of absorbent fibers, and a superabsorbent material has typically been combined with the absorbent fibers to increase the liquid absorbent capacity. The absorbent core has been formed in a substantially rectangular shape. The absorbent core has also been formed in an hourglass shape, a T-shape, or similar configuration with a reduced absorbent width in the central crotch region for improved fit and comfort.

Such conventional absorbent articles have included elasticized leg openings, elasticized waistbands, and elasticized inner containment flaps at the leg and waist areas of the article to improve fit and reduce leakage. In addition, the articles have included wicking layers or distribution layers for directing and moving liquids to appointed regions of the absorbent structure. Typically, such distribution layers extend from one waistband end of the article, through a crotch region of the article, and into a longitudinally opposed waistband end of the article.

Such conventional absorbent articles, however, have not provided desired levels of liquid distribution and desired efficiencies of liquid storage. The absorbent articles frequently leak before the total liquid absorbent capacity of the entire article is fully utilized. A contributing cause of this premature leakage is an inability of the absorbent system to adequately transport discharged liquids from a liquid-intake area of the article to more remote, end regions of the absorbent structure. The absorbent systems have not transported adequate amounts of liquid at adequate transport rates away from the intake area of the article, particularly during the course of multiple liquid discharges into article. Typically, the article intake area includes the relatively narrower crotch region of the absorbent system. As a result, the crotch region of the absorbent becomes excessively saturated, is unable to accommodate additional discharges of liquid, and prematurely leaks. While this is happening, the absorbent material positioned at the more remote areas of the absorbent, particularly at the back waistband region of the absorbent, remains only partially utilized.

Consequently, there remains a need for absorbent structures which can provide desired combinations of liquid distribution, controlled liquid storage and leakage resistance.

BRIEF DESCRIPTION OF THE INVENTION

Generally stated, the present invention provides an absorbent article, such as the representatively shown diaper, has a longitudinal direction, a lateral direction, a first waistband portion, a second waistband portion and an intermediate portion interconnecting the first and second waistband portions. The article includes a backsheet layer; a liquid permeable top sheet layer; and an absorbent structure sandwiched between the backsheet and topsheet layers. The absorbent structure includes a retention portion having a first retention section and a longitudinally opposed second retention section. A liquid distribution, waist belt component has a belt first end region, a belt second end region and a belt medial region interconnecting the belt first and second end regions. The belt first end region is joined to the article in liquid communication with the first retention section, and the distribution belt component has sufficient lateral length to extend along a wearer's waist area to position the belt second end region in liquid communication with the second retention section when the article is worn.

The various aspects of the present invention can be employed alone or in combination, and can advantageously provide a distinctive absorbent structure which can more efficiently store liquid in areas that are remote from the intake region of the absorbent structure. The configurations of the invention can more effectively reduce a wet-thickness of the absorbent structure, can reduce the bulkiness in the crotch region of the article, and can improve the fit, comfort and aesthetics of the article. As a result, the absorbent structures and articles of the invention can provide improved fit, reduced leakage, and a more efficient utilization of the total amount of absorbent material in the article.

BRIEF DESCRIPTION OF THE DRAWINGS

The present invention will be more fully understood and further advantages will become apparent when reference is made to the following detailed description of the invention and the drawings, in which:

FIG. 5 representatively shows a first or bodyside layer of a multiple layer retention portion which can be employed with the present invention;

FIG. 5A representatively shows a second or outward side layer of the multiple layer retention portion which can be employed with the present invention;

DETAILED DESCRIPTION OF THE INVENTION

Figure 1:
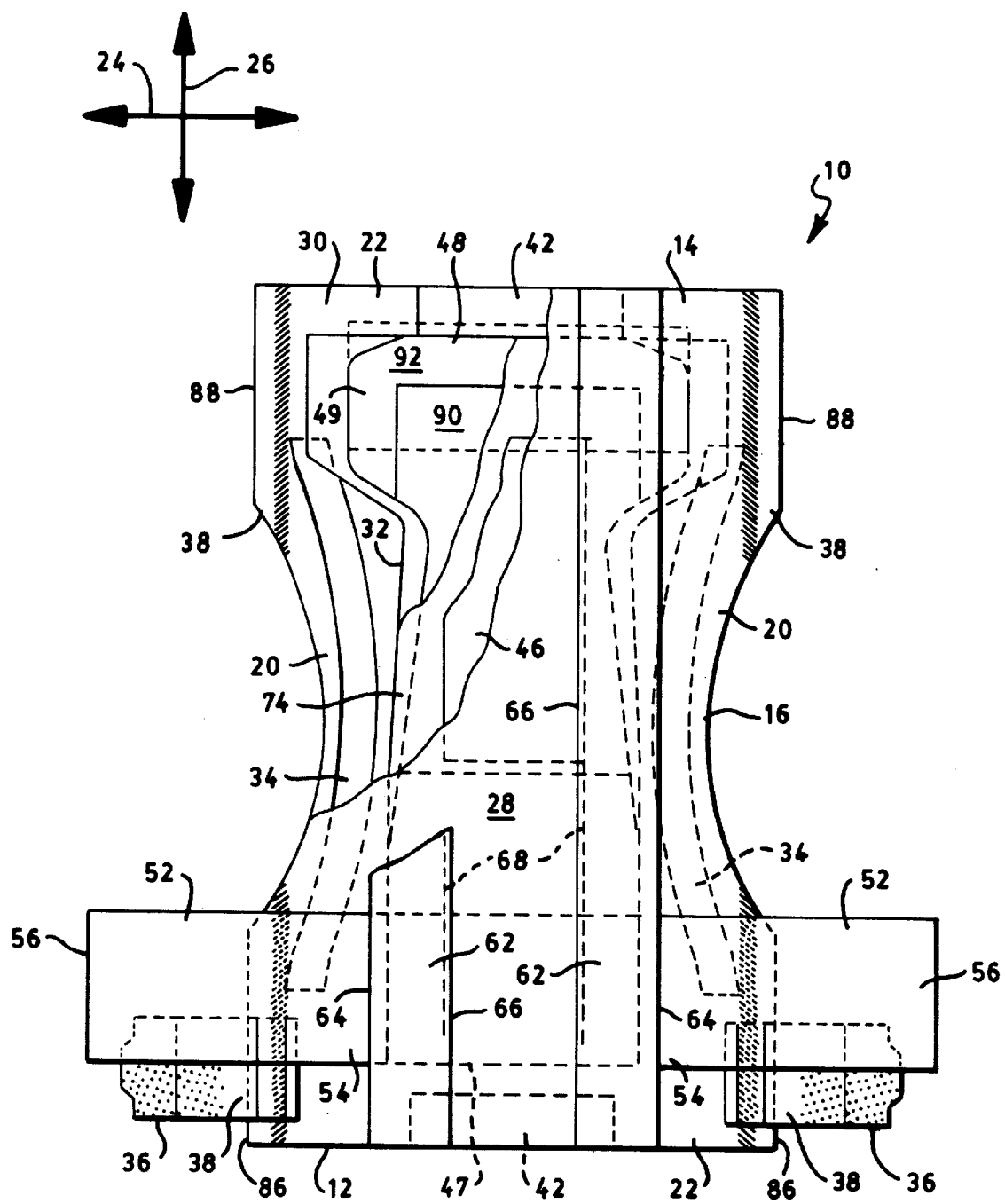
FIG. 1 representatively shows a partially cut-away, plan view of the inward side of an article of the invention which incorporates the distribution belt system.

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

In conventional absorbent articles, such as conventional diapers, the back portion of the absorbent core is typically underutilized in current diapers with wearers, e.g. infants, who sleep on their stomachs. Similarly, when the wearers sleep on their back, the front portion of the absorbent is typically underutilized. Such conventional articles have not allowed a desired transfer of liquid from the front portion of the absorbent to the back portion of the absorbent (or vice-versa, as the case may be). A contributing factor is that the liquid impermeable backsheet or outercover typically becomes interposed between the overlapping, front and back portions of the absorbent when the diaper is applied and fastened during use.

The present invention advantageously incorporates distinctive design modifications at the front and/or back waistband and ear regions of the article. The modifications can provide a more efficient and more effective liquid communication between the front and back waistband sections of the absorbent. In addition, the article of the invention can provide an improved, interfacial connection between a distinctive liquid distribution member and its associated liquid storage member. The connection can allow a substantially free transfer of liquid across an interface between the distribution member and storage member without excessive liquid-barrier interference from another material component. With reference to FIGS. 1, 2, 3 and 4, an absorbent article, such as the representatively shown diaper 10, has a longitudinal direction 26; a lateral direction 24; a first waistband portion 12, such as the representatively shown back waistband portion; a second waistband portion 14, such as the representatively shown front waistband portion; and an intermediate portion 16 interconnecting the first and second waistband portions. The article 10 includes a backsheet layer 30, a liquid permeable top sheet layer 28, and an absorbent structure 32 sandwiched between the backsheet and topsheet layers. The absorbent structure includes a retention portion 48 having a first retention section 47 and a longitudinally opposed, second retention section 49. The article also includes at least one liquid distribution, waist belt component 52 having a belt first end region 54, a belt second end region 56, and a belt medial region 58 which interconnects the belt first and second end regions. The belt first end region 54 is joined to the article in liquid communication with the first retention section 47, and the distribution belt component 52 has sufficient lateral length to extend along a wearer's waist area to position the belt is second end region 56 in liquid communication with the second retention section 49 when the article is worn.

The various aspects of the invention, alone or in combination, can provide an improved mechanism for distributing liquid to thereby increase the amount and rate of liquid transport away from the target intake area of the article to more remote and less utilized areas of the absorbent structure. This can more effectively and more efficiently reduce the level of liquid saturation in the target intake area during the time period following the liquid discharge into the target area, and can maintain area in a better condition for absorbing subsequent intakes of liquid. The invention can provide an improved ability to store liquid in areas away from the central target intake region of the product, and can help reduce the wet-thickness of the absorbent structure and improve crotch fit. The article of the invention can provide an improved ability to control locations where liquid is stored, and can help improve comfort and aesthetics.

In particular, the distribution belt components can transport liquid directly from the first (e.g. front) section of the retention portion to the second (e.g. back) section of the retention portion along a shorter liquid conductive path which avoids passing through the intermediate, crotch portion of the absorbent structure. Additionally, the article of the invention can provide improved liquid transport without increasing the mass of distribution material in the crotch region and without increasing the crotch bulk and degrading the fit.

The distribution belt components can also help reduce competition for the transportable liquid between the absorbent components (e.g. the superabsorbent material and fluff) by separating and spacing apart the distribution material from the storage and retention material. As a result, the distribution material in the distribution belt component can be relatively more effective, as compared to the same mass of distribution material added to the main portion of the absorbent structure.

The article of the invention can, for example, be a garment provided by the representatively shown disposable diaper 10. In desired aspects of the invention, the first article portion can, for example, provide a first, rear or back waistband portion 12, and the second article portion can provide a second, front waistband portion 14. In addition, the article can have an intermediate or crotch portion 16 which interconnects between the first and second waistband portions 12 and 14, respectively. The diaper can further include a backsheet layer 30, a liquid permeable topsheet layer 28 connected and assembled in facing relation with the backsheet layer, and an absorbent structure, such as a structure which includes an absorbent body 32 having the retention portion 48. The absorbent structure is sandwiched between the backsheet and topsheet layers, and is operably held therebetween. In addition, a fastening system, such as the system including fasteners 36, may be employed to interconnect the first waistband portion 12 with the second waistband portion 14 to hold the article on a wearer.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects between the front and rear waistband section and provides a diaper crotch region which is typically positioned between the legs of the wearer. The article has an appointed fastener landing zone member 50 which is disposed on the outward surface of the article. In the configuration shown in FIGS. 1, 2 and 3, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

Figure 2:
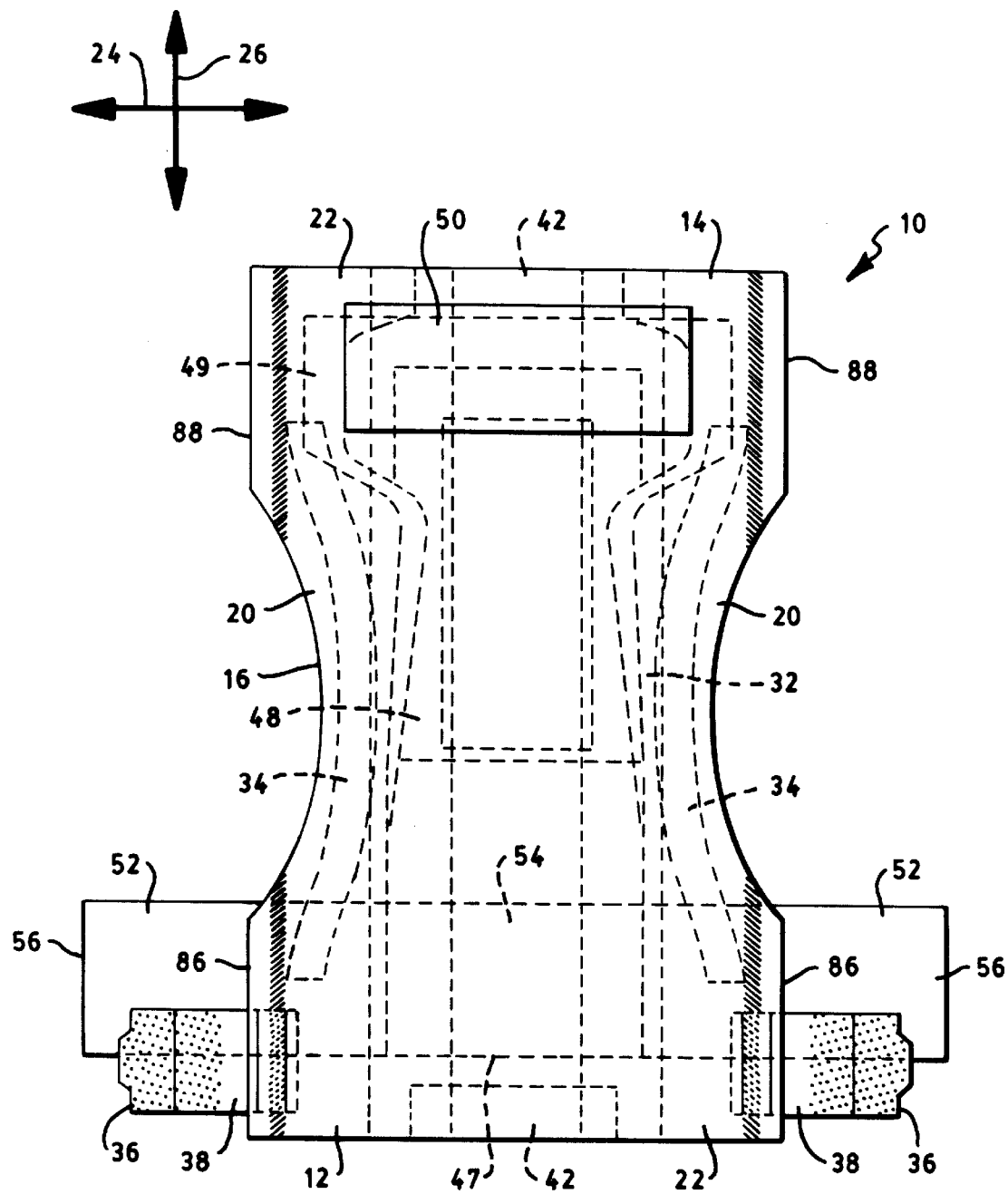
FIG. 2 representatively shows a plan view of the outward side of the article illustrated in FIG. 1.
Figure 3:
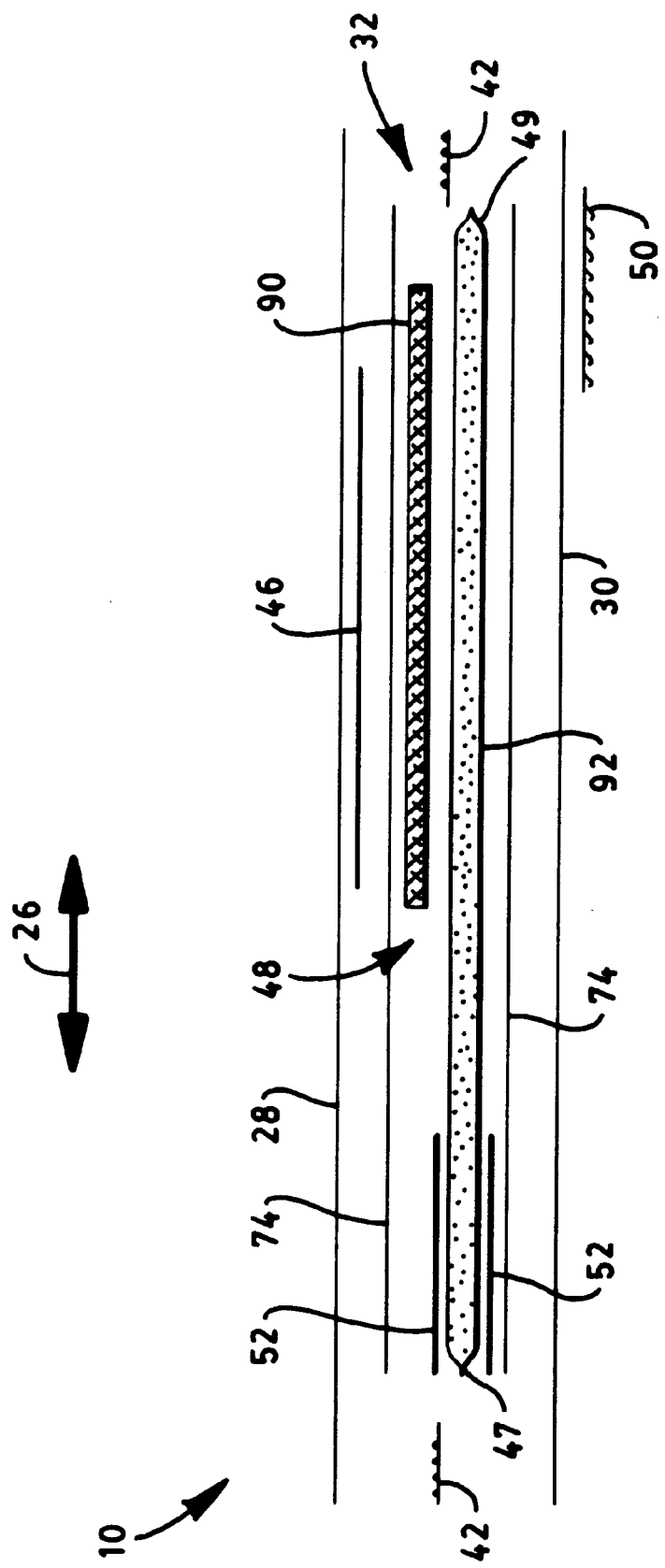
FIG. 3 representatively shows an expanded schematic, longitudinal cross-sectional view of the article illustrated in FIG. 1.
Figure 4:
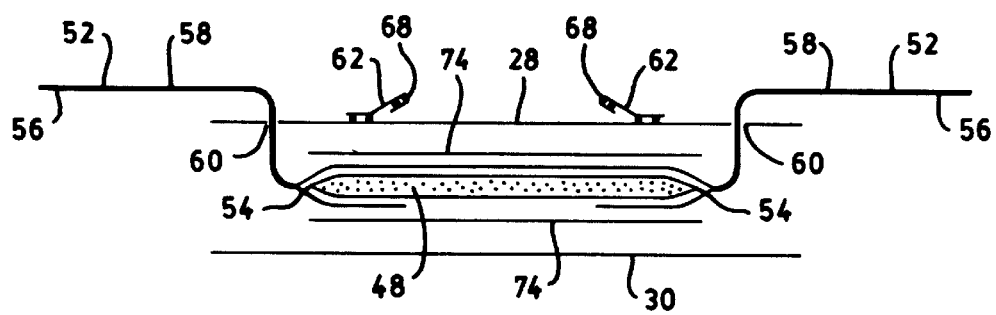
FIG. 4 representatively shows an expanded schematic, lateral cross-sectional view of the article illustrated in FIG. 1 taken along a section of the distribution belt system.

FIGS. 1 and 2 show typical plan views of the representative disposable diaper 10 in its generally flat-out, uncontracted state (i.e., with substantially all elastic induced gathering and contraction removed). In FIG. 1, the bodyside surface of the diaper which contacts the wearer is facing the viewer, and portions of the structure are partially cut away to more clearly show the interior construction of the diaper article. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article is configured to face away from the wearer's body when the article is placed about the wearer.

The diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with an appointed storage or retention portion 48 of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which corresponds to U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which corresponds to U.S. Pat. No. 5,595,618. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. The backsheet 30 prevents the exudates contained in absorbent body 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene blown film layer and a 0.7 ounce per square yard (23.8 g/M$^2$) polypropylene spunbond material (2 denier fibers) layer. A material of this type has been employed to form the outer-cover of a HUGGIES SUPREME disposable diaper, which is commercially available from Kimberly-Clark Corporation. The backsheet 30 typically provides the outer cover of the article. Optionally, however, the article may include a separate outer cover component or member which is additional to the backsheet.

The backsheet 30 may alternatively include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention where a component, such as the backsheet 30 or the containment flaps 62, are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 g/m$^2$ and density of about 0.06 gm/cc. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which the topsheet 28 is directly joined to the backsheet 30 by affixing the topsheet 28 directly to the backsheet 30, and configurations wherein the topsheet 28 is indirectly joined to the backsheet 30 by affixing the topsheet 28 to intermediate members which, in turn, are affixed to the backsheet 30. The topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment means may also be employed to suitably interconnect, assemble and/or affix together the various other component parts of the articles which are described herein.

The absorbent body 32 provides an absorbent structure which can include the retention portion 48, such as the shown absorbent pad composed of selected hydrophilic fibers and high-absorbency particles, which holds and stores absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of the absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, the absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may include absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic is complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the synthetic polymer material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is at least a minimum of about 400 g/m². The average basis weight can alternatively be at least about 500 g/m², and optionally can be at least about 550 g/m² to provide improved performance. In certain aspects of the invention, the average composite basis weight can be not more than a maximum of about 1200 g/m². Alternatively, the basis weight can be not more than 1000 g/m², and optionally can be not more than about 800 g/m² to provide further improved performance.

The retention portion 48, as employed in the various arrangements of the invention, can be composed of a single layer or may be composed of a plurality of two or more layers. With regard to the various aspects of the retention portion described herein, it should be appreciated that each of the aspects, alone or in combination with other aspects, can pertain to the overall retention portion, or may pertain to an individual layer within a multi-layer retention portion.

The absorbent materials in the retention portion 48 are able to hold and store absorbed liquids. In the representatively shown configuration, for example, the retention section 49 located in an appointed front waistband portion of the article can provide an initial retention section, and the longitudinally opposed retention section 47 in the appointed back waistband portion of the article can provide a supplemental retention section. In an alternative configuration, the retention section 47 can provide the initial retention section, and the retention section 49 can provide the supplemental retention section.

In the shown arrangement, the supplemental retention section (e.g. the first retention section 47) in the back waistband portion of the retention portion is constructed to operatively desorb and retain the liquid transported to the supplemental retention section from the initial retention section (e.g. the second retention section 49) by way of the distribution belt component 52. Accordingly, the capacity of the first retention section should be great enough to store all the liquid transported to it during the expected loading cycle of the product. In general, the capacity can be at least a minimum of about 50 g of 0.9% saline. The capacity of the supplemental retention section can alternatively be at least about 75 g of saline, and optionally can be at least about 100 g of saline to provide improved performance. In other aspects of the invention, the capacity of the supplemental retention section can be not more than a maximum of about 500 g of saline. Alternatively, the capacity can be not more than 400 g of saline, and optionally can be not more than about 300 g of saline to provide further improved performance.

In further aspects of the invention, the absorbent capacities of the retention sections 47 and 49 can be selectively configured to control or limit the amount of liquid storage at appointed locations to provide an improved distribution profile of stored liquid across the retention portion 48.

The retention materials, particularly the absorbent materials in the appointed supplemental retention section should be configured to provide a capillary suction value which is greater than the capillary forces holding the transported liquid within the distribution belt components 52 to allow an effective transfer of liquid from the distribution belt components into the supplemental retention section. Thus, the capillary suction value of the supplemental retention section is desirably greater than about 15 cm.

Examples of suitable materials can include blends of wettable (less than about 30 degree contact angle) pulp fibers (less than about 17 $\mu$m diameter) and at least about 20% by weight superabsorbent at a web density of about 0.17 g/cm³.

The retention portion 48 may include a separately provided stabilizing material, which is additional to the cellulosic fibers and superabsorbent polymer material, and is in an amount which is at least a minimum of about 0.5 wt %, as determined with respect to a total weight of the retention portion. The amount of stabilizing material can alternatively be at least about 1 wt %, and optionally can be at least about 2 wt % to provide improved performance. In other aspects of the invention, the amount of stabilizing material can be not more than a maximum of about 50 wt %. Alternatively, the amount of stabilizing material can be not more than 35 wt %, and optionally can be not more than about 20 wt % to provide further improved performance.

Another aspect of the present invention can include a retention portion 48 which contains stiffened cellulose fibers in an amount which is at least a minimum of about 10 wt %. The amount of stiffened cellulose can alternatively be at least about 20 wt %, and optionally can be at least about 25 wt % to provide improved performance. In other aspects of the invention, the amount of stiffened cellulose can be not more than a maximum of about 90 wt %. Alternatively, the amount of stiffened cellulose can be not more than 80 wt %, and optionally can be not more than about 60 wt % to provide further improved performance.

A particular aspect of the invention can include a retention portion 48 which contains hydrophilic, crimped, synthetic fiber in an amount which is at least a minimum of about 10 wt %. The amount of hydrophilic, crimped, synthetic fiber can alternatively be at least about 20 wt %, and optionally can be at least about 25 wt % to provide improved performance. In other aspects of the invention, the amount of hydrophilic, crimped, synthetic fiber can be not more than a maximum of about 90 wt %. Alternatively, the amount of hydrophilic, crimped, synthetic fiber can be not more than 80 wt %, and optionally can be not more than about 60 wt % to provide further improved performance.

In desired aspects, the retention portion 48 can have a dry thickness which is at least a minimum of about 0.1 cm, as determined under a restraining pressure of 1.38 KPa. The dry thickness can alternatively be at least about 0.15 cm, and optionally can be at least about 0.2 cm to provide improved performance. In other aspects of the invention, the dry thickness can be not more than a maximum of about 1.2 cm. Alternatively, the dry thickness can be not more than 1 cm, and optionally can be not more than about 0.8 cm to provide further improved performance.

In still other aspects, the retention portion 48 can have a dry density which is at least a minimum of about 0.05 g/cm$^3$, as determined under a restraining pressure of 1.38 KPa. The dry density can alternatively be at least about 0.075 g/cm$^3$, and optionally can be at least about 0.1 g/cm$^3$ to provide improved performance. In other aspects of the invention, the dry density can be not more than a maximum of about 0.4 g/cm$^3$. Alternatively, the dry density can be not more than 0.3 g/cm$^3$, and optionally can be not more than about 0.25 g/cm$^3$ to provide further improved performance.

With reference to FIGS. 1, 3, 5 and 5A, the absorbent article can further include a retention portion 48 having a plurality of retention layers, such as a first retention layer 90 and at least a second retention layer 92. In the representatively shown configuration, for example, the first retention layer 90 is a bodyside layer positioned relatively closer to the wearer's body, and the second retention layer 92 is an outward side layer positioned relatively further from the wearer's body. The multiple layer retention portion can provide a selected combination of multiple functions, such as intake, distribution, and retention. An absorbent article having an absorbent system which includes multiple layer portions can be distinctively configured to cause the multiple layers to cooperative interact in a manner which preferentially controls the location of liquid in one or more designated or appointed layer regions. The intake capability of the absorbent system, particularly the intake capability of the absorbent core, can be maintained or improved over conventional systems by keeping a primary, intake layer region of the absorbent system at low saturation levels through as many insults of the product as possible, while providing optimum intake performance through appropriate control of the composite properties. The relatively low level of liquid saturation in this intake layer region provides void volume for the incoming insult as well as a high permeability, thus increasing the intake rate of the absorbent system as a whole. The intake layer region can advantageously be configured to provide an appropriately high level of capillary tension to adequately control of the movement of liquid and substantially avoid undesired leakage. This low saturation, intake layer region is desirably employed in addition to a separately provided surge management portion or layer, and can provide an intake functionality which is additional to that provided by the material of the surge layer. The saturation of the intake layer can be maintained at a low level by preferentially concentrating the liquid in a distribution layer region. This localization of the liquid within a designated, layer region can increase the potential of this layer region to move and distribute liquid through capillary action, due to the relatively higher saturation level and increased amount of liquid available in the designated layer.

In particular aspects of the invention, the first retention layer 90 can include a controlled-rate superabsorbent, and a high bulk wood pulp fiber or other woven or nonwoven fibrous material with pore size distributions which allow for a rapid uptake of liquid while maintaining the liquid within the structure until it can be absorbed by the relatively outward layer region or layer regions of the absorbent. The components in the first layer region portion 90 can be positioned to substantially cover the appointed, intake target area of the product, the area where liquids, such as urine, are introduced into the absorbent structure. A particular controlled-rate superabsorbent can be a superabsorbent wherein the individual superabsorbent particles are treated with a hydrophobic coating to provide a selected delay in the absorption of aqueous liquids into the particles. For example, the superabsorbent may be a coated particulate superabsorbent. The particles have absorbent centers composed of a partial sodium salt of a cross-linked polyproponic acid (prepared by the process described in U.S. Pat. No. 5,629,377), and the particle centers are covered with a hydrophobic silicone elastomer coating. A representative controlled-rate superabsorbent of this type is available from DOW Chemical Company, a business having offices in Midland, Mich., U.S.A.

An alternative controlled-rate superabsorbent can be configured with relatively large particle sizes to provide particles having a low, surface area to volume ratio which thereby produces the desired absorbency rate. The controlled-rate superabsorbent particles can also have a substantially spherical or other three-dimensional shape which operatively generates the desired low ratio of surface-area-to-volume and delayed absorbency rate.

In addition, the bulk chemistry of the superabsorbent polymer can be modified to provide the desired, delayed absorbency rate. For example, the controlled-rate superabsorbent may incorporate an anionic polyelectrolyte which is reversibly crosslinked with a polyvalent metal cation. A water soluble complexing agent may be configured to reverse the crosslinking.

Alternative controlled-rate superabsorbents can be encased by a coating or other treatment which operatively slows the diffusion of liquid into the superabsorbent particles, or repels liquid in a manner which provides the desired delayed absorbency rate. The coatings or treatments may be elastic or inelastic, and the coating or treatment may be hydrophobic or hydrophilic. The coatings may erode, dissolve, or crack in a controlled fashion to provide the desired absorbency characteristics. Optionally, the absorbency rate may be limited and/or controlled by modifying the neutralization rate of the selected superabsorbent material, or by modifying or otherwise controlling the chemical mechanism employed to produce the neutralization of the selected superabsorbent.

High bulk fibers are those which impart improved bulk retention and/or recovery from deformation. The high bulk fibers can particularly provide wet bulk retention, and/or wet recovery from deformation when the fibers are incorporated into materials which become wetted. Examples of suitable high bulk fibers include synthetic, thermoplastic fibers, synthetic fibers composed of natural polymers such as cellulose, and natural fibers, as well as combinations thereof. The resiliency of fibers composed of natural polymers can be enhanced by chemical crosslinking and/or by imparting kink and/or curl to the fiber.

Alternatively, the first retention layer 90 can be composed of a fibrous material based on a woven or nonwoven technology. As in the previous aspects of the invention, these materials will be configured to provide maximum void volume and permeability while maintaining enough capillary tension to control the movement of the liquid and not allow leakage to occur. For example, the absorbent cores of the present invention could incorporate nonwoven materials as functional components for the first retention layer region 90. Bonded carded webs are examples of particular fibrous materials that could be configured to provide an adequate balance of permeability and capillarity. Through the selection of staple fiber options, one can create a composite structure that will preferentially saturate the second retention layer 92. This can be done either through physical structuring of the top layer, controlled surface chemistry or both. The porosity of fibrous structures can be determined by the specific fibers and fiber sizes selected. Fiber selection can also impact the capillarity of the material. In desired arrangements, the first retention layer 90 can be configured to provide a top, bodyside layer of the absorbent structure, and the second retention layer 92 can provide a bottom, outward side layer of the absorbent structure.

Suitable carded structures have been produced from a variety of fiber types and from an assortment of fiber sizes. Fibers can be produced from both synthetic and naturally occurring materials. Desirably, the fibers for the first layer 90 can be very wettable, and natural cellulosic materials such as rayon or cotton may be employed. Synthetic fibers such as polyester and polyamide offer limited wettability which could be enhanced with hydrophilic finishes or treatments. While fiber diameters of a fairly wide range occur in carded nonwovens the desired structure would contain fibers with equivalent diameters less than 25 microns. A carded material for the first layer 90 can be produced in a weight range from about 50 to 200 grams per square meter (gsm, or $g/m^2$) at a density of about 0.03 $g/cm^3$ or less. The density of the fibrous material will ultimately depend upon the method used to bond or stabilize the web.

Carded webs can be stabilized through various methods. Incorporation of thermoplastic staple fibers is used in some cases so that the structure might be bonded using heat and pressure. Proper application of heat and pressure in thermal bonding can result in a structure that is stabilized with very specific permeability and capillarity. Carded structures can also be stabilized using chemical resins or adhesives. Again, selection of the specific resin or adhesive, add-on amounts and curing will facilitate control of the final web properties which impact permeability and capillarity. Weltability can be impacted by the choice of chemical resin system for bonding. Carded structures can be mechanically stabilized using water, needling, air or other means to entangle fibers. Again, these processes can be controlled in such a way that physical attributes of the material are as desired.

Particular aspects of the invention can incorporate a spunbonded fabric with properties similar to that described above. Other aspects of the invention may also include a selected zoning of the fiber size, basis weight, or other features of the material to provide desired performance attributes. In addition to carded fibrous webs and meltspun fibrous webs, airlaid fibrous materials may also be used.

In particular aspects of the invention, the first layer region 90 can be a top, bodyside layer which can typically extend over a longitudinally medial section of the overall core area, but may optionally extend over the entire core area, if desired. The top layer typically is the layer which is optimized for intake performance and may or may not provide desired levels of liquid wicking or distribution performance. The first layer region typically can have a minimum basis weight of not less than about 100 $g/m^2$, and desirably can have a basis weight of not less than about 200 $g/m^2$. In further aspects, the first layer region typically can have a maximum basis weight of not more than about 500 $g/m^2$, and desirably has a basis weight of not more than about 450 $g/m^2$.

The first layer portion typically includes a minimum of not less than about 25% fibrous material by weight (wt %), and desirably includes not less than about 40% fibrous material. In other aspects, first layer portion typically can include a maximum of not more than about 80% fibrous material, and desirably can include not more than about 60% fibrous material. The fibrous material may be natural or synthetic in nature. The fibrous material can have a minimum fiber size, particularly a fiber diameter, of at least about 4 microns ($\mu$m), and desirably has a fiber size of at least about 10 microns. In further aspects, fibrous material can have a maximum fiber size of not more about 20 microns, and desirably has a fiber size of not more than about 15 microns.

The first layer portion can also contain a minimum of not less than about 20% of superabsorbent material by weight, and desirably contains not less than about 30% superabsorbent. In additional aspects, the first layer portion can include a maximum of not more than about 75% superabsorbent material, and desirably can include not more than about 50% superabsorbent. The superabsorbent material can have a minimum, dry particle size of not less than about 140 microns, and desirably has a dry particle size of not less than about 300 microns. In other aspects the superabsorbent material can have a maximum, dry particle size of not more than about 1000 microns, and desirably can have a dry particle size of not more than about 700 microns. The superabsorbent material can also have a Modified Absorbency Under Load, MAUL, value of not less than about 20 g/g, and desirably can have a MAUL value of not less than about 25 g/g. Additionally, the MAUL value can be up to about 30 g/g, or more to provide improved benefits. In further aspects, the superabsorbent material can have a particular absorbency rate, Tau ($\tau$) value, of at least about 0.8 minutes, and can have a Tau value of up to about 40 minutes.

The Modified Absorbency Under Load value and the Tau value of a superababsorbent material can be determined in accordance with the procedures which are described in detail in U.S. patent application Ser. No. 09/096,652 entitled LAYERED ABSORBENT STRUCTURE by R. D. EVERETT et al. (attorney docket No. 13,505.1) which was filed Jul. 12, 1998, the entire disclosure of which is incorporated herein by reference.

The first layer region 90 of the retention portion 48 can typically have a minimum average density of at least about 0.03 g/cm$^3$, and desirably has a density of at least about 0.05 g/cm$^3$. In other aspects, the first layer region can have a maximum average density of not more than about 0.4 g/cm$^3$, and desirably can have a density of not more than about 0.2 g/cm$^3$. The first layer region includes any issue layers which are used to hold together the materials positioned in the first layer region or which act as a carrier mechanism. For example, several layers of tissue may be employed to hold superabsorbent material which is laminated between the tissue layers.

The various configurations of the invention can include any operative intake material in the selected layers of the absorbent structure. Examples of suitable intake materials can include the materials described in U.S. patent application Ser. No. 754,414 entitled MULTIFUNCTIONAL ABSORBENT MATERIAL AND PRODUCTS MADE THEREFROM, by R. Anderson et al., and filed Nov. 22, 1996 (attorney docket No. 12,442); and in U.S. Provisional Patent Application Ser. No. 068,534 entitled PULP AND SUPERABSORBENT COMPOSITE FOR IMPROVED INTAKE PERFORMANCE, by L. H. Sawyer et al., and filed Dec. 23, 1997 (attorney docket No. 13,041). The entire disclosures of these documents are incorporated herein by reference in a manner that is consistent herewith.

In other aspects of the invention, the second retention layer 92 can be composed of a mass or matrix of hydrophilic fibers, such as wood pulp fibers, and a selected quantity of superabsorbent gelling material, such as Coosa 1654 wood pulp and Stockhausen FAVOR 880 superabsorbent. These materials will typically be blended or otherwise combined such that about 20–80 wt % of the composite is composed of superabsorbent particles. Modifications of this material may also be made to provide improved product performance. These modifications can include the use of modified pulp fibers to generate improvements in the distribution of liquid, or the use of a stabilization technique to control the structure and generate improved wicking performance. Potential methods of stabilization include, but are not limited to, the use of a binder material, such as KYMENE binder material or some other cross-linking agent, or the introduction of heat activated binder fibers. Structure stabilization is a technology that is used to maintain the structure or minimize changes to the structure of a material or a composite of materials when the materials are exposed to external or internal forces. Various techniques, such as the incorporation of thermoplastic binder fibers, chemical cross-linking agents (such as Kymene), and the like, as well as combinations thereof, may be employed to stabilize the absorbent structures.

Any material which is operatively configured with the ability to provide improved distribution of liquid away from the target area can provide the desired functional results. These materials can be composed of a laminate which includes superabsorbent particles and at least one fibrous web which is particularly configured to exhibit an improved wicking flux performance. Suitable arrangements of the second layer region 92 can include, but are not limited to, laminations of particulate or fibrous superabsorbent webs with cellulosic tissue materials, or any other stabilized, fibrous web.

The distributing layer can advantageously provide particular important functions. A first function includes the retention and movement of liquid away from the target area, and a second function is to provide enough short term (during liquid insult) superabsorbent capacity to make up for the shortfall in void volume associated with thin product executions. Structural elements of this layer region include the content of superabsorbent polymer material (SAP), the component basis weights, and the component densities.

The component materials in the second layer region 92 can be provided in various operative amounts, basis weights, densities, etc. For example, the second primary layer region may have a substantially uniform basis weight. Additionally, the second layer region 92 can constitute about 25%–100% of the overall, composite basis weight of the absorbent core structure at any one location, and may typically have a density in the range of about 0.1 g/cm$^3$ to 0.3 g/cm$^3$. In still other aspects, the second layer region 92 may include a plurality of two or more component sub-layer regions, wherein each of the component sub-layer regions has a selected combination of physical and functional characteristics.

The second layer portion typically includes not less than about 50% fibrous material by weight, and desirably includes not less than about 60% fibrous material. In other aspects, second layer portion typically can include not more than about 80% fibrous material, and desirably can include not more than about 75% fibrous material. The fibrous material may be natural or synthetic in nature. The fibrous material can have a fiber size, particularly a fiber diameter, of at least about 4 microns, and desirably has a fiber size of at least about 10 microns. In further aspects, fibrous material can have a fiber size of not more about 20 microns, and desirably has a fiber size of not more than about 15 microns. In addition, the fibrous material can have a contact angle with water of not more than about 65 degrees, and desirably has a contact angle with water of not more than about 50 degrees.

The second layer portion can also contain not less than about 20% of superabsorbent material, by weight, and desirably contains not less than about 30% superabsorbent. In additional aspects, the second layer portion can include not more than about 50% superabsorbent material, and desirably can include not more than about 40% superabsorbent. The superabsorbent material can have a dry particle size of not less than about 140 microns, and desirably has a dry particle size of not less than about 300 microns. In other aspects the superabsorbent material can have a dry particle size of not more than about 1000 microns, and desirably can have a dry particle size of not more than about 700 microns. The superabsorbent material can also have a MAUL value of not less than about 20 g/g, and desirably can have a MAUL value of not less than about 25 g/g. Additionally, the MAUL value can be up to about 30 g/g, or more to provide improved benefits. In still other aspects, the superabsorbent material can have a Tau value of at least about 0.67 minutes, and can desirably have a Tau value of at least about 2 minutes In particular aspects of the invention, the superabsorbent material in the first layer region 90 may be configured to have a Tau value which is about twice the Tau value of the superabsorbent located in the second layer region 92 (Tau-value-ratio of about 2:1)., The Tau-value-ratio can alternatively be at least about 2.5:1, and optionally, can be at least about 3:1 to provide desired characteristics. In additional aspects, the combination of superabsorbent materials in the first and second layer regions can be configured to provide a Tau-value-ratio of up to about 10:1, and alternatively, the combination of superabsorbent materials can be configured to provide a Tau-value-ratio of up to about 40:1, or more.

The second layer region 92 can typically have an average density of at least about 0.1 9/cm$^3$, and desirably, can have a density of at least about 0.15 g/cm$^3$. In other aspects, the second layer region can have an average density of not more than about 0.3 g/cm$^3$, and desirably can have a density of not more than about 0.25 g/cm$^3$. In particular aspects, the average density can be about 0.2 g/cm$^3$. The second layer region includes any tissue layers which are used to hold together the materials positioned in the second layer region or which act as a carrier mechanism. For example, several layers of tissue may be employed to hold a layer of superabsorbent material which is laminated between the tissue layers.

Further descriptions of the various configurations of the invention are provided in U.S. patent application Ser. No.09/096,652 of R. Everett et al., entitled LAYERED ABSORBENT STRUCTURE, and filed Jun. 12, 1998 (attorney docket No. 13,505.1); U.S. patent application Ser. No. 09/097,285 of R. Everett et al., entitled LAYERED ABSORBENT STRUCTURE WITH A ZONED BASIS WEIGHT, and filed Jun. 12, 1998(attorney docket No. 13,506.1); U.S. patent application Ser. No. 09/096,653 of R. Everett et al., entitled LAYERED ABSORBENT STRUCTURE WITH A HETEROGENEOUS LAYER REGION, and filed Jun. 12, 1998 (attorney docket No. 13,507.1); and U.S. patent application Ser. No. 09/097,029 of R. Everett et al., entitled LAYERED ABSORBENT STRUCTURE WITH A ZONED BASIS WEIGHT AND A HETEROGENEOUS LAYER REGION, and filed Jun. 12, 1998 (attorney docket No. 13,508.1). The entire disclosures of each of these documents are incorporated herein by reference in a manner that is consistent herewith.

Alternatively, the second retention layer 92 can be composed of other suitable fibrous webs may include wet laid tissue, airlaid materials incorporating staple synthetic and natural fibers, or treated meltblown webs, as well as the types of fibrous webs employed to construct the first layer region 90. Another class of materials which can be used to provide improved functionality are laminates of superabsorbent particles or fibrous webs and wettable, open cell foams.

To improve the containment of the high-absorbency, superabsorbent material, the entire absorbent body structure 32 or selected portions of the absorbent structure can include an overwrap, such as wrap sheet 74. The wrap sheet can be placed immediately adjacent and around the selected regions of the absorbent body 32 and may be bonded to the absorbent structure and to the various other components of the article. The wrap sheet can be a layer of absorbent material which covers the major bodyside and outerside surfaces of the entire absorbent body or selected layers of the absorbent body and preferably encloses substantially all of the peripheral edges of the selected region of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the selected region of the absorbent body. Accordingly, both the linear and the inwardly curved portions of the lateral side edges of the wrap sheet would be closed about the selected regions of the absorbent body. In such an arrangement, however, the end edges of the wrap sheet may not be completely closed around the end edges of the selected region of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of the selected region of the absorbent body 32. Such a configuration of the wrap sheet can, for example, facilitate the formation of a substantially complete sealing and closure around the peripheral edges of the selected region of the absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

The article of the invention can advantageously include at least one distinctive "Waist belt", liquid distribution member or component 52 which is operatively configured and joined to the article. The distribution belt component can, for example, be connected and/or secured to the article at the regions of its front and back waistband portions, and can provide an operative, liquid-conducting path between appointed regions of the front and back waistband sections of the retention portion 48 when the article is secured on the wearer and worn. In the various arrangements of the distribution belt components 52, the relatively remote and previously underutilized areas of the retention portion 48 can receive more liquid and can provide more efficient absorbency. In particular, the system of distribution belt components 52 can advantageously transport liquid from more highly saturated sections to less saturated sections of the absorbent retention portion. The distribution belt component 52 can be constructed to uptake liquid from an appointed, initial-intake section of the retention portion 48 and operatively move and transport the liquid to an appointed, supplemental section of the retention portion.

Figure 6:
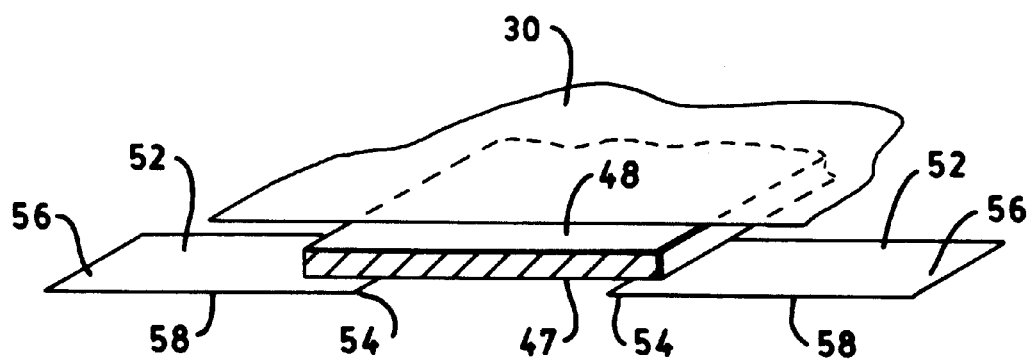
FIG. 6 representatively shows a partial, expanded, isometric view of a waistband portion of an article having a laterally opposed pair of distribution belt components.
Figure 6A:
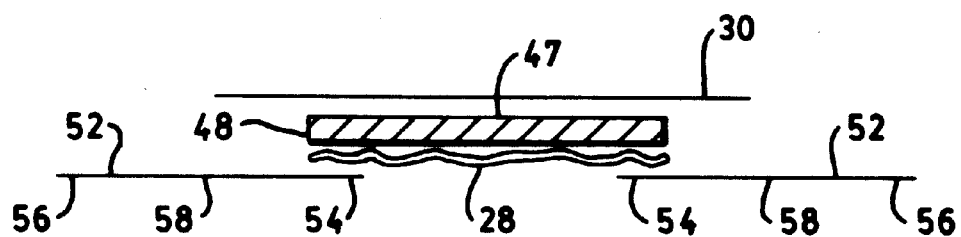
FIG. 6A representatively shows a partial, expanded, lateral cross-sectional view of a waistband portion of another article of the invention having a laterally opposed pair of distribution belt components.
Figure 6B:
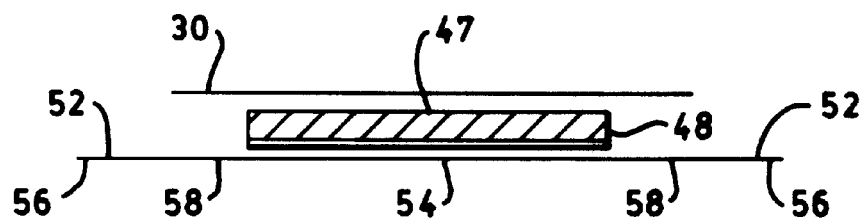
FIG. 6B representatively shows a partial, expanded, lateral cross-sectional view of a waistband portion of an article of the invention having an integrated distribution belt system.

With reference to FIGS. 6, 6A and 6B, each distribution belt component 52 has a belt component first end region 54, a belt component second end region 56, and a belt component medial region 58. Desirably, the article can include a cooperating pair of laterally opposed distribution belt components 52, with one belt component appointed for placement along each side of a wearer. Each distribution belt component may be a separately provided member, as representatively shown in FIGS. 6 and 6A. In an alternative arrangement representatively shown in FIG. 6B, the pair of distribution belt components may be integrally formed and joined to each other to provide an integrated belt system at an appointed waistband portion of the article, such as the back waistband portion.

An operative, liquid conductive attachment between the distribution belt component 52 and the appointed, initial-intake section of the retention portion is configured to provide a functional interfacial connection which provides the desired transfer of liquid from the initial retention section and into the distribution belt 52. Similarly, an operative, liquid conductive attachment between the distribution belt component 52 and the appointed, supplemental section of the retention portion 48 is configured to provide a functional interfacial connection which provides the desired transfer of liquid from the distribution belt component 52 and into the supplemental retention section.

Figure 7:
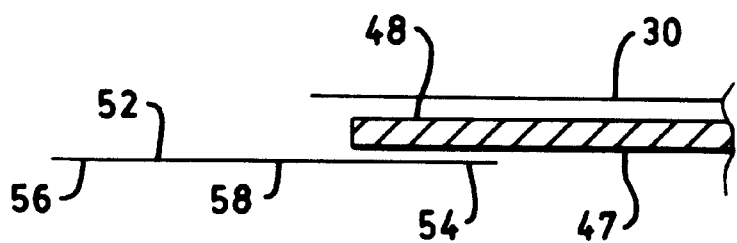
FIG. 7 representatively shows an expanded, schematic cross-sectional view taken through a partial article at the location of a distribution belt component having a substantially direct interface and contact with the retention portion.
Figure 7A:
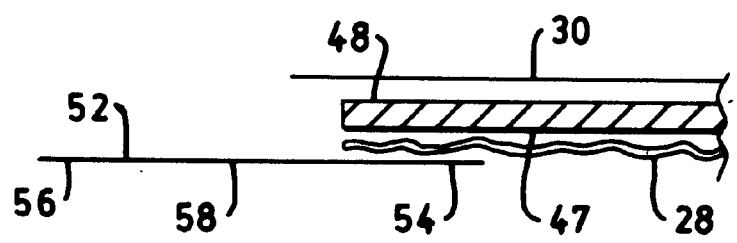
FIG. 7A representatively shows an expanded, schematic cross-sectional view taken through a partial article at the location of another distribution belt component having an indirect interface and contact with the retention portion.

With reference to FIG. 7, the belt first end region 54 of each belt component 52 can be joined in a substantially direct contact with the first retention section 47. With alternative configurations, the belt first end region 54 may be joined in an indirect contact with the first retention section 47, as illustrated in FIG. 7A.

Figure 8:
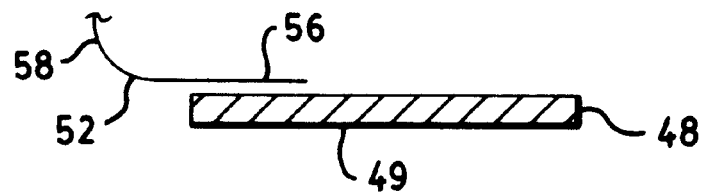
FIG. 8 representatively shows an expanded, schematic cross-sectional view taken through a partial article at the location of a distribution belt component having a substantially direct contact with the front section of the retention portion.

With reference to FIG. 8, the article can be configured and arranged to provide a substantially direct contact between the belt second end region 56 and the second retention section 49. The article can alternatively be configured to provide an indirect contact between the second end region 56 of each distribution belt component 52 and the second section 49 of the retention portion, as representatively shown in FIG. 8A. In a particular aspect of the invention, the selected system of distribution belt components 52 can be configured to allow the second end regions 56 of the distribution belt components to effectively overlap each other at the location of the second retention section 49, as representatively shown in FIG. 8B.

In further aspects of the invention, the article can include one or more structural modifications to help provide the desired liquid-communicating connection between each distribution belt component and its appointed sections of the retention portion 48. Particular aspects of the invention can include a topsheet layer 28 which is modified to help provide liquid-communicating contact between the distribution belt components 52 and the retention portion 48. In particular arrangements, the topsheet may include a slit or other aperture or opening therethrough to allow a more direct contact between the distribution belt components 52 and the appointed sections of the retention portion 48. For example, with reference to FIGS. 1, 2 and 4, the article can include the placement of openings or apertures 60, such as the representatively shown slits, through the inner topsheet 28 at an appointed, article waistband portion (e.g. the shown back waistband portion 12). Each distribution belt component 52 can be inserted through its associated, corresponding aperture 60 to contact the underlying section of the retention portion 48 (e.g. the shown first retention section 47). The first end region 54 of each distribution belt component 52 can be configured to extend through the slit aperture in a first waist band portion of the topsheet layer 28 to acquire and form the desired, liquid-communicating interface with the first retention section 47.

In another arrangement, the topsheet layer 28 may be foreshortened or otherwise modified at a selected waistband portion to effectively remove the presence of the topsheet layer from the areas of the retention portion 48 that are appointed to be over-laid by the corresponding end regions of the distribution belt components 52. For example with reference to FIG. 8, the topsheet layer 28 may be foreshortened or otherwise modified at the front waistband portion to effectively remove the presence of the topsheet layer from the areas of the second retention section 49 that are appointed to be over-laid by the corresponding, second end regions 56 of the distribution belt components 52.

Figure 8A:
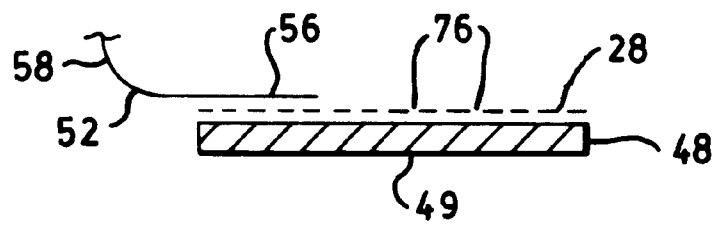
FIG. 8A representatively shows an expanded, schematic cross-sectional view taken through a partial article at the location of another distribution belt component having an indirect contact with a front section of the retention portion.
Figure 8B:
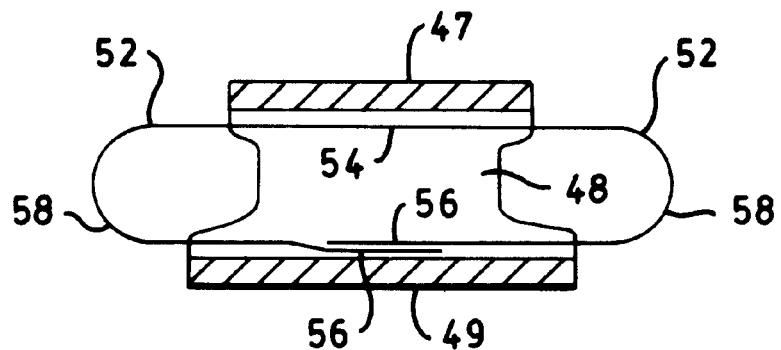
FIG. 8B representatively shows an expanded, schematic cross-sectional view taken through a partial article at the location of a distribution belt assembly wherein the distribution belt components are integrally connected at a back section of the retention portion and have an overlapping connection at the front section of the retention portion.

Another aspect of the invention can include a topsheet layer 28 having at least one cooperating aperture 76, and desirably a plurality of apertures, located in and distributed along an appointed waist band portion of the topsheet layer 28 to provide selected open areas which allow a substantially direct contact between the corresponding end regions of the distribution belt components and the retention portion 48. As illustrated in FIG. 8A, for example, the second, front waist band portion of the topsheet layer 28 can include a multiplicity of apertures 76 to provide selected areas of substantially direct contact between the belt second end region 56 and the second retention section 49.

Alternatively, the region of the article above the appointed section of the retention portion can be constructed without the inner topsheet 28 and the distribution belt component 52 can be constructed with soft, topsheet materials attached to a body-contacting side of the distribution belt component. When the diaper is applied to the wearer the distribution belt component 52 can be contacted to the desired section of the retention portion. Since the inner topsheet is absent from the contact area, the topsheet does not interfere with the interface which provides the desired liquid transfer. The side of the distribution belt which is covered with topsheet material is oriented inwardly toward the wearer and provides its associated softness and dryness benefits.

The distribution belt component 52 can be composed of at least one web of natural and/or synthetic materials which can rapidly transport liquid against gravitational forces from more saturated sections of the retention portion, and can then deposit the liquid into relatively less saturated sections of the retention portion. In particular configurations, each distribution belt component 52 can include a plurality of two or more webs that are cooperatively combined together.

The distribution belt component 52 can have a generally rectangular shape. Alternatively, the distribution belt component can have a curved or otherwise contoured shape which is configured to increase the amount of direct contact with the more highly saturated sections of the retention portion 48, such as the sections of the retention portion that are positioned in or proximate the intermediate, crotch region of the article, and can thereby enhance the transport of liquid away from the crotch region.

The waist distribution belt components may desirably brought into contact with the retention portion at a location which is away from the appointed target intake region of the absorbent structure to help maintain the intake properties of the absorbent system. For example, at least a portion of the distribution belt component 52 can be located adjacent an appointed outward facing surface of the retention portion, or adjacent an appointed outward facing surface of a selected layer of the retention portion 48.

Operative, liquid-conductive interfaces are desirably provided between the cooperating sections of the distribution belt components 52 and the retention portion 48 to achieve desired levels of liquid communication and system functionality. In particular aspects of the invention, a surface-to-surface contact area between each distribution belt component 52 and its correspondingly joined sections of the retention portion can be at least about one square inch. Adhesive or mechanical bonds can, for example, be employed to help provide suitable attachments and liquid-conductive interfaces between the distribution belt components and the corresponding sections of the retention portion.

Figure 9:
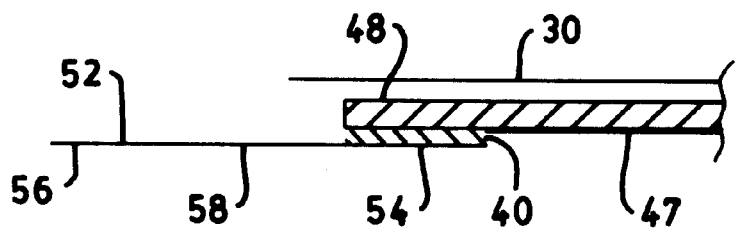
FIG. 9 representatively shows an expanded, schematic cross-sectional view taken through a partial article at the location of a distribution belt component having a transport attachment with the retention portion.
Figure 9A:
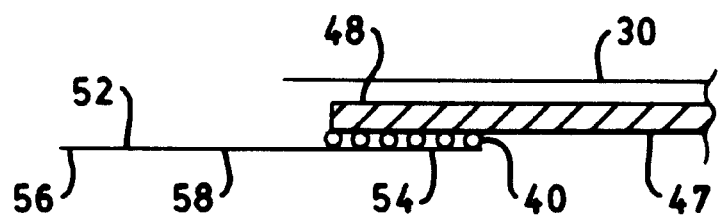
FIG. 9A representatively shows an expanded, schematic cross-sectional view taken through a partial article at the location of a distribution belt component having another transport attachment with the retention portion.

With reference to FIGS. 9 and 9A, an operative transport attachment 40 between each appointed end region (e.g. first end region 54) of the distribution belt component 52 and its corresponding section of the retention portion 48 (e.g. first retention section 47) is configured to provide an operative, interfacial connection between the distribution belt component and its corresponding section of the retention portion to allow an efficient transfer of liquid into and out from each distribution belt component 52. The transport attachment 40 substantially maintains an operative, liquid-conducting, surface contact between the distribution belt component and their corresponding sections of the retention portion. The operative contact can, for example, be due to the pressure exerted on the interface between the distribution belt component and the retention portion when the article is applied to the wearer. Other transport attachments 40 can include adhesive bonds, such as those provided by the adhesives employed in adhesive fastening tapes, or other mechanical bonds. For training pants or pre-fastened diapers, the transport attachments 40 could additionally include thermal or ultrasonic bonds. Elastomeric properties provided to either the distribution belt component and/or its associated transport attachments would facilitate the placement and securement of the article on the wearer.

The material composition and the structure of the distribution belt component 52 can contribute to the rate and amount of liquid movement through the distribution system of the invention. The liquid movement can include capillary wicking through the internal material structure of the distribution belt component. The distribution belt component can include webs composed of natural and/or synthetic materials that have the capability to transport a liquid to a selected height at a selected rate and flux. Desired aspects of the invention can incorporate a distribution belt component 52 which exhibits a distinctive Vertical Liquid Flux value. In particular, the distribution belt component can have the capability to transport a liquid having a surface tension of 72 dynes/cm to a height of 15 cm and provide a Liquid Flux value of at least a minimum of about 0.002 gm/min/gsm/in (grams per minute per gsm per inch). The Liquid Flux value represents a wicking property of a material expressed in terms of the amount of liquid in grams transported to a 15 cm vertical height per minute per one gsm (g/m$^2$) basis weight of material per one inch (2.54 cm) of material width.

In particular aspects, the distribution belt component can have a Vertical Liquid Flux value of at least about 0.0025 gm/min/gsm/in. Alternatively, the distribution belt component can have a Vertical Liquid Flux value of at least about 0.0050 gm/min/gsm/in, and optionally, the distribution belt component can have a Vertical Liquid Flux value of at least about 0.1 gm/min/gsm/in to provide improved performance. When the distribution belt component exhibits a Vertical Liquid Flux value of less than about 0.002 gm/min/gsm/in, the material has little capability to move liquid against gravity and tends to retain the liquid in its structure at the front of the product. In other aspects, each waist belt distribution component 52 can be sized and dimensioned to provide sufficient liquid transport from the target intake area to the supplemental storage area without interfering with the fit of the product about the wearer's waist For example, the length measured in the longitudinal machine direction of the distribution belt component can be not more than about four inches, and desirably, can be not more than about two inches for a "STEP 3" sized diaper (for a 16–28 lb infant). It is desirable that the distribution belt component be capable of transporting at least about 20 grams of liquid per hour, and more preferably at least about 40 grams of liquid per hour. The thickness of the waist belt should be minimized to maintain a trim fit at the waist. In particular aspects, the distribution belt component can have a thickness of less than about 10 mm, and optionally can have a thickness of less than about 5 mm to provide improved performance.

In other aspects of the invention, the distribution belt component 52 can be composed of a wettable hydrophilic woven or nonwoven fabric composed of natural fibers, synthetic fibers or combinations thereof, with a basis weight which is at least a minimum of about 50 g/m$^2$ (gsm). The basis weight can alternatively be at least about 75 g/m$^2$, and optionally can be at least about 100 g/m$^2$ to provide improved performance. In other aspects of the invention, the basis weight can be not more than a maximum of about 800 g/m$^2$. Alternatively, the basis weight can be not more than 600 g/m$^2$, and optionally can be not more than about 500 g/m$^2$ to provide further improved performance.

In further aspects of the invention, the distribution belt component 52 can be composed of a wettable hydrophilic woven or nonwoven fabric composed of natural fibers, synthetic fibers or combinations thereof material with a density which is at least a minimum of about 0.05 g/cm$^3$ (g/cm$^3$). The density can alternatively be at least about 0.075 g/cm$^3$, and optionally can be at least about 0.1 g/cm$^3$ to provide improved performance. In other aspects of the invention, the density can be not more than a maximum of about 0.4 g/cm$^3$. Alternatively, the density can be not more than 0.3 g/cm$^3$, and optionally can be not more than about 0.25 g/cm$^3$ to provide further improved performance. For the purposes of the present description, the densities are determined under a restraining pressure of 1.38 KPa.

In particular aspects, the distribution belt component 52 can have a Vertical Liquid Flux value of not less than a minimum of about 0.002 gm/min/gsm/in. Alternatively, the distribution belt component can have a Vertical Liquid Flux value of not less than about 0.0025 gm/min/gsm/in, and optionally, the distribution belt component can have a Vertical Liquid Flux value of not less than about 0.1 gm/min/gsm/in to provide further benefits.

The Vertical Liquid Flux value can be determined with a Vertical Liquid Flux test method. In this test, a sample strip of material approximately 2 inches (5 cm) by 15 inches (38 cm) is placed vertically such that when the sample strip is positioned above a liquid reservoir at the beginning of the test, the bottom of the sample strip will touch the liquid surface. The liquid used was a 8.5 g/l saline solution. The relative humidity should be maintained at about 90 to about 98 percent during the evaluation. The sample strip is placed above the known weight and volume of liquid and a stopwatch started as soon as the bottom edge of the sample strip touches the surface of the solution. The vertical distance of the liquid front traveling up the sample strip and the liquid weight absorbed by the sample strip at various times are recorded. The time versus liquid front height is plotted to determine the Wicking Time at about 15 centimeters. The weight of the liquid absorbed by the sample strip from the beginning of the evaluation to about 15 centimeters height is also determined from the data. The Vertical liquid Flux value of the sample strip at a particular height is calculated by dividing the grams of liquid absorbed by the sample strip by each of: the basis weight (gsm) of the sample strip; the time, in minutes, needed by the liquid to reach the particular height; and the width, in inches, of the sample strip. The equilibrium capillary tension is considered to be the height of liquid at the end of 30 minutes. Using the test method described in detail herein, the Vertical Liquid Flux value of a material reflects the capillary tension of the distribution belt component.

Various structures can be employed to provide the desired Vertical Liquid Flux to the overall distribution belt component. For example, the distribution belt component can be provided with a uniform or non-uniform wet-formed or dry-formed laminate structure Alternatively, the distribution belt component can be provided with homogeneous or heterogeneous wet-formed or dry-formed non-layered composite structure Various materials can be employed to provide the desired Vertical Liquid Flux value to the distribution belt component. For example, the distribution belt component of the article can be composed of a woven fabric and nonwoven webs, foams and filamentous materials. For example, the distribution belt component may be a nonwoven fabric layer composed of a meltblown or spunbond web of polyolefin, polyester, polyamide (or other web forming polymer) filaments. Such nonwoven fabric layers may include conjugate, biconstituent and homopolymer fibers of staple or other lengths and mixtures of such fibers with other types of fibers. The distribution belt component can be a coform, a bonded carded web, an airlaid web or a wetlaid pulp structure composed of natural and/or synthetic fibers (e.g. KRATON binder fiber available from Shell Chemical Company, a business having offices located in Houston, Tex.), as well as combinations thereof.

In particular aspects of the invention the distribution belt component includes a laminate having one or more layers of a liquid-permeable material which operates as a distribution material, such as layers of an uncreped-through-air-dried (UCTAD) sheet material. For example, the sheet material may be a fibrous tissue, and desired configurations can incorporate the selected UCTAD material in the second primary layer region of the absorbent core.

Generally stated, the UCTAD material is a cellulosic tissue material produced in accordance with the process described in U.S. patent application Ser. No. 08/310,186 entitled WET RESILIENT WEBS by F. J. Chen et al. which was filed Sep. 21, 1994 (attorney docket No. 11,700), the entire disclosure of which is incorporated herein by reference.

Suitable UCTAD materials can provide a wicking property characterized by a liquid flux, at a height of 15 cm, which is at least 0.002 grams of liquid per minute per basis weight of 1 g/m$^2$, per 1 inch of material width. The UCTAD material has a basis weight of at least about 50 g/m$^2$, and has a density within the range of about 0.08–0.5 g/cm$^3$. Desirably, the density can be within the range of about 0.1–0.3 g/cm$^3$. The permeability of the UCTAD is within the range of about 50–1000 Darcys. The UCTAD material has a dry tensile strength of at least 5000 grams of force per 1 inch of the material when plied to a total basis weight of 200 g/m$^2$ Suitable UCTAD materials are described in U.S. patent application Ser. No. 08/767,645 filed Dec. 17, 1996 by J. Dutkiewicz et al., and entitled ABSORBENT STRUCTURE FOR LIQUID DISTRIBUTION (attorney docket No. 12,267), the entire disclosure of which is incorporated by reference in a manner that is consistent herewith.

Figure 10:
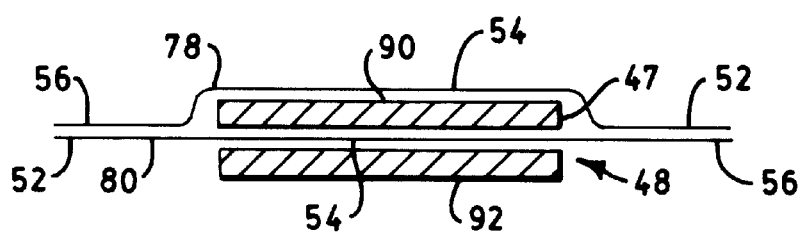
FIG. 10 representatively shows an expanded, schematic cross-sectional view taken through a partial article at a location where a multi-layer distribution belt component is combined with a retention portion.
Figure 10A:
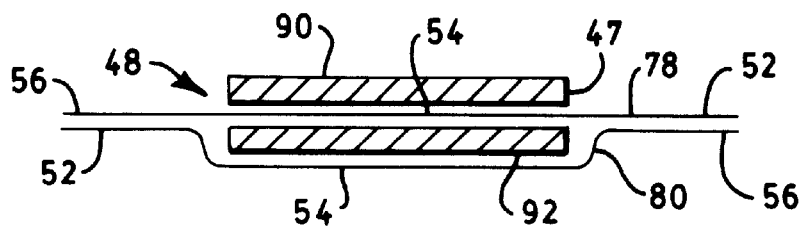
FIG. 10A representatively shows an expanded, schematic cross-sectional view taken through a partial article at a location where a multi-layer distribution belt component is operatively combined with a retention portion in another configuration.
Figure 10B:
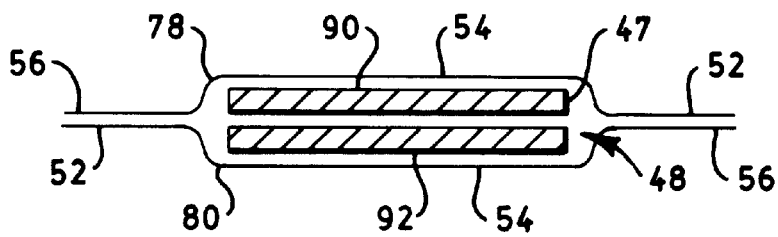
FIG. 10B representatively shows an expanded, schematic cross-sectional view taken through a partial article at a location where a multi-layer distribution belt component is operatively combined with a retention portion in another configuration.
Figure 10C:
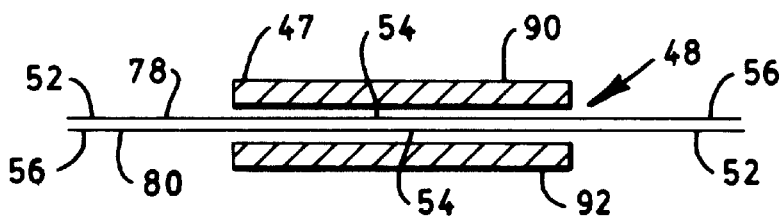
FIG. 10C representatively shows an expanded, schematic cross-sectional view taken through a partial article at a location where a multi-layer distribution belt component is operatively combined With a retention portion in another configuration.
Figure 10D:
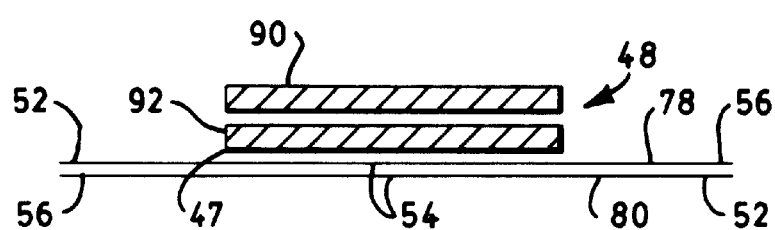
FIG. 10D representatively shows an expanded, schematic cross-sectional view taken through a partial article at a location where a multi-layer distribution belt component is operatively combined with a retention portion in another configuration.
Figure 10E:
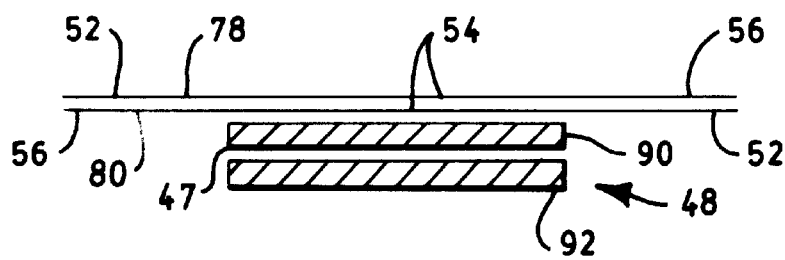
FIG. 10E representatively shows an expanded, schematic cross-sectional view taken through a partial article at a location where a multi-layer distribution belt component is operatively combined with a retention portion in another configuration.

With reference to FIGS. 10 through 10E, the distribution belt component of the article may be a laminate, and can have a first belt layer 78 and at least a second belt layer 80. In particular configurations of the invention, the first belt layer 78 may be positioned along an appointed body side of the belt component 52. The first belt layer 78 can be composed of woven fabric and nonwoven webs, foams and filamentary materials, as well as combinations thereof. For example, the distribution layer may be a nonwoven fabric layer composed of a meltblown or spunbond web of polyolefin, polyester, polyamide (or other web forming polymer) filaments. Such nonwoven fabric layers may include conjugate, bi-constituent and homopolymer fibers of staple or other lengths, and mixtures of such fibers with other types of fibers. The distribution layer can be a coform, a bonded carded web, an airlaid web or a wetlaid pulp structure composed of natural and/or synthetic fibers (e.g. KRATON binder fiber), as well as combinations thereof. The first belt layer can desorb liquid (an ability to intake urine from the wearer's skin and the target zone), distribute the liquid, and release the liquid (an ability to give up urine to remote regions in the product).

The second belt layer 80 may, for example, be positioned along an appointed outward side of the distribution belt component 52. The second belt layer 80 can be composed of woven fabric and nonwoven webs, foams and filamentary materials. For example, the distribution layer may be a nonwoven fabric layer composed of a meltblown or spunbond web of polyolefin, polyester, polyamide (or other web forming polymer) filaments. Such nonwoven fabric layers may include conjugate, bi-constituent and homopolymer fibers of staple or other lengths and mixtures of such fibers with other types of fibers. The distribution layer can be a coform, a bonded carded web, an airlaid web or a wetlaid pulp structure composed of natural and/or synthetic fibers (e.g. KRATON binder fiber) or a combination thereof. The first belt layer can provide the following functionalities: desorption or intake (of urine from the wearers skin and the target zone), distribution and release (ability to give up urine to remote regions in the product).

With reference to FIGS. 10, 10A and 10B, the first and second belt layers 78 and 80 of the distribution belt component 52 can be configured to sandwich at least a portion of the retention portion 48 (e.g. the first retention section 47) therebetween. Optionally, the first and second belt layers 78 and 80 of the distribution belt component 52 can be configured to sandwich at least a portion of the second retention section 49 therebetween.

In particular configurations of the invention, the retention portion 48 can include the first retention layer 90 and at least the second retention layer 92, and the distribution belt component can include the first belt layer 78 and at least the second belt layer 80. In addition, at least a portion of the first belt layer 78 can be interposed between the first retention layer 90 and the second retention layer 92, as representatively shown in FIGS. 10A and 10C. In another aspect of the invention, at least a portion of the second belt layer 80 can be positioned substantially adjacent the second retention layer 92 and interposed between the second retention layer and the back sheet layer 30.

With reference to FIG. 10D, the first belt layer 78 can be located on a bodyside surface of the second belt layer 80, and can be configured to be interposed between the second belt layer and the wearer when the article is worn. In another configuration of the invention (e.g. FIG. 10E), the first belt layer 78 can be located on a bodyside of the second belt layer 80, and can be configured to contact the wearer when the article is worn. In alternative arrangements, the first belt layer 78 can be interposed between the retention portion 48 and the topsheet layer 28. In still other optional configurations, the second belt layer 80 can be interposed between the first retention layer 90 and the second retention layer 92.

In particular aspects, the waist belt, liquid distribution components 52 may also contain superabsorbent material. Desirably, the superabsorbent polymers have a controlled—rate of liquid absorption. The desired controlled rate superabsorbent can have a Tau value which is at least a minimum of about 0.8 min. Desirably, the superabsorbent Tau value is at least about 2 min, and can be at least about 4 min to provide improved performance. In still other aspects the Tau value can be up to about 40 minutes or more. It is furthermore desirable that the waist belt contain not more than 40% of superabsorbent material, by weight, and preferably not more than 20% superabsorbent material, by weight, to maintain effective liquid distribution.

In their various aspects and configurations, the distribution belt components 52 can provide a shorter, more direct, and less competitive route or pathway to direct liquid away from the crotch intake region and transport the liquid to a more remote section of the retention portion 48, such as the illustrated first retention section 47 at the back waistband portion of the article. The transportation of liquid can be achieved through capillary liquid movement within the material structure of the distribution waist belt component 52. The movement path from the second retention section 49, through the distribution belt component and into the first retention section 47 is shorter and more effective than the conventional path from the second retention section through the crotch region of the absorbent and then into the first retention section. Additionally, this invention can provide a more efficient liquid transport by separating and reconfiguring the distribution function from the retention function.

Diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which corresponds to U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which corresponds to U.S. Pat. No. 5,490,846. Other suitable surge management materials are described in U.S. patent application Ser. No. 754,417 filed Nov. 22, 1996 and entitled HETEROGENEOUS SURGE MATERIAL FOR ABSORBENT ARTICLES by R. Dodge et al, (attorney docket No. 12,120). The entire disclosures of these documents are hereby incorporated by reference in a manner that is consistent herewith.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward a longitudinally extending centerline of the diaper. In particular arrangements, the curvature of the elastics may not be configured or positioned symmetrically relative to the laterally extending centerline of the diaper. The curved elastics may have an inwardly bowed and outwardly bowed, reflex-type of curvature, and the lengthwise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a corresponding one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), which corresponds to U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753, 646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18, 1995 (attorney docket No. 11,091), the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

With reference to FIGS. 1 and 2, the article of the invention can include a laterally opposed pair of fasteners 36 which, when the article is worm, are positioned outward of the distribution belt components 52 (relative to the wearer) and are configured to operatively secure the article on the wearer.

To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

The various configurations of the invention can indude at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a corresponding one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the back waistband section 12.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical fastening element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include a loop type of mechanical fastening element; and the complementary, second fastening component, which is operatively joined and attached to the appointed landing zone member, can include a hook type of fastening element.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 (attorney docket No. 12,563) which corresponds to U.S. Pat. No. 5,624,429 which issued Apr. 29, 1997, the entire disclosure of which is hereby incorporated by reference in a manner which is consistent herewith.

Each fastener tab 36 can have a variety of rectilinear or curvilinear shapes and planforms, as well as combinations thereof. For example, as illustrated in the representatively shown arrangements, the fastener tab can have a contoured, bell-shape. Alternatively, the fastener tab can have a quadrilateral, generally rectangular shape. In addition, the longitudinally extending, laterally outward, terminal edge of the fastener tab may be substantially straight. Optionally, the longitudinally extending, laterally outward, terminal edge of the fastener tab may have only a limited amount of waviness.

In the various configurations of the invention, the desired first fastener component can be a hook material which provides hook-type engagement members. An example of a suitable hook material is a micro-hook material which is distributed under the designation VELCRO HTH 829, and is available from VELCRO U.S.A., Inc., a business having offices in Manchester, New Hampshire. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units). Other suitable hook materials can include VELCRO HTH 858, VELCRO HTH 851 and VELCRO HTH 863 hook materials.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N. C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web boy bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996 (attorney docket No. 12,232); the entire disclosure of which is incorporated herein by reference in a manner that is consistent herewith.

In the various configurations of the invention, the loop material need not be limited to a discrete or isolated patch on the outward surface of the article. Instead, the loop material can, for example, be provided by a substantially continuous, outer fibrous layer which is integrated to extend over substantially the total exposed surface area of a cloth-like outer cover employed with the desired article.

In the various arrangements of the invention, the engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch of the width of engagement between the first and second fastener components. In further arrangements, the fastening engagement may provide a peel force value of not less than about 100 gmf/inch to provide improved advantages. In desired configurations, the fastening engagement may provide a peel force value of not less than about 200 gmf per inch of the width of engagement between the first and second fastener components. Alternatively, the peel force is not less than about 300 gmf/inch, and optionally is not less than about 400 gmf/inch to further provide improved benefits. In other aspects, the peel force is not more than about 1,200 gmf/inch. Alternatively, the peel force is not more than about 800 gmf/inch, and optionally is not more than about 600 gmf/inch to provide improved performance.

The engagement force between the selected first fastener component and its appointed and cooperating second fastener component may additionally provide a shear force value of not less than about 400 gmf per square inch of the area of engagement between the first and second fastener components. Alternatively, the shear force is not less than about 1,000 gmf/in$^2$, and optionally, is not less than about 1,700 gmf/in$^2$. In further aspects, the shear force can be up to about 4,400 gmf/in$^2$, or more. Alternatively, the shear force is not more than about 3,900 gmf/in$^2$, and optionally is not more than about 3,500 gmf/in$^2$ to provide improved performance.

Desirably, the securing engagement between the first and second fastener components should be sufficient to prevent a disengagement of the fastener tab 36 away from the landing member 50 when the fastener tab 36 is subject to a tensile force of at least about 3,000 grams when the tensile force is applied outwardly along the lateral direction, aligned generally parallel with the plane of the backsheet layer 30 of the article.

Each of the fastener components and fastening elements in the various constructions of the invention may be operably attached to its supporting substrate by employing any one or more of the attachment mechanisms employed to construct and hold together the various other components of the article of the invention. It should be readily appreciated that the strength of the attachment or other interconnection between the substrate layer and the attached fastening component should be greater than the peak force required to remove the fastener tab 36 from its releasable securement to the appointed landing member of the article.

The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

Figure 11:
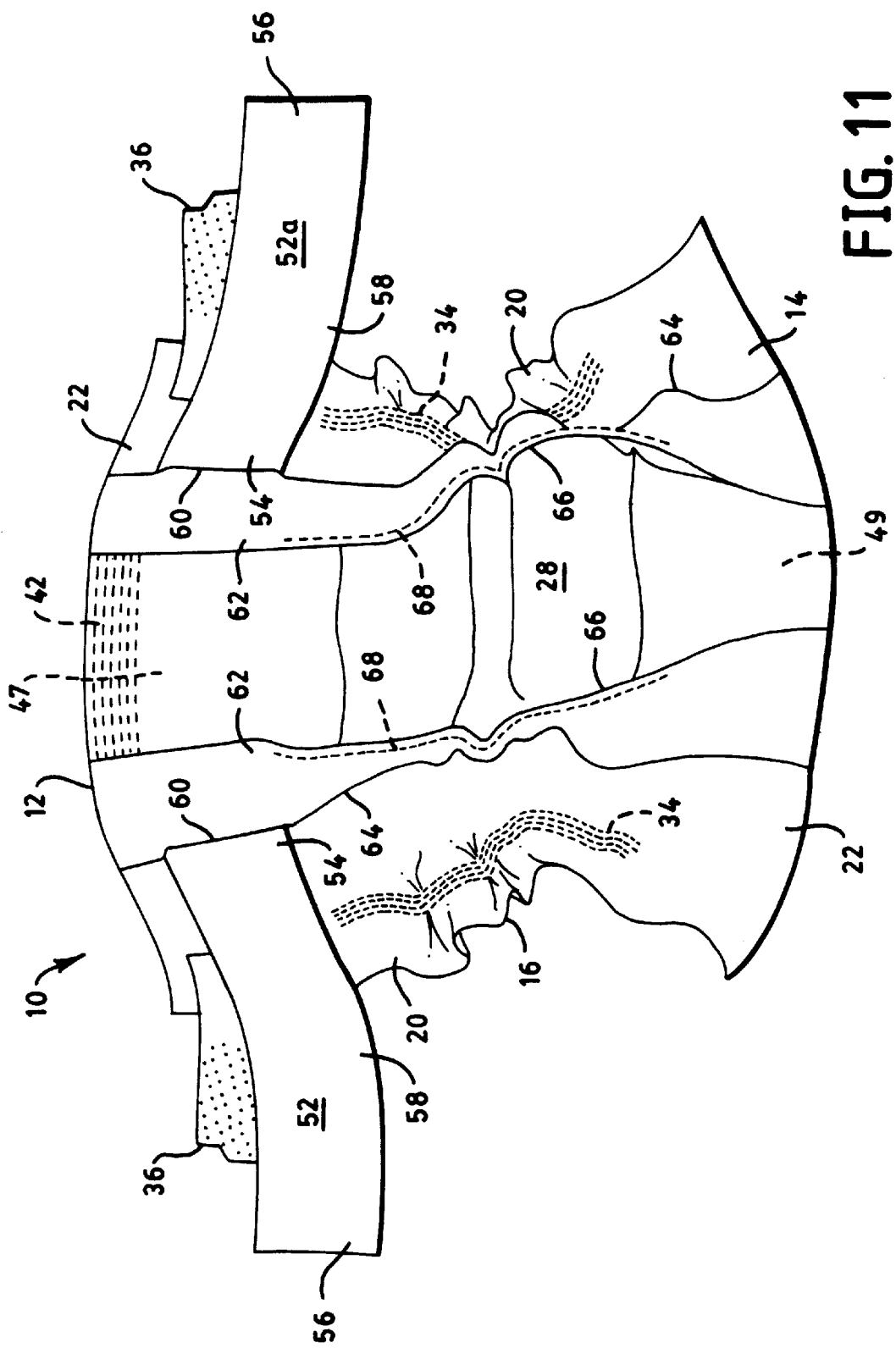
FIG. 11 representatively shows a perspective view of an open article of the invention having a laterally opposed pair of distribution belt components arranged prior to placement on a wearer.
Figure 11A:
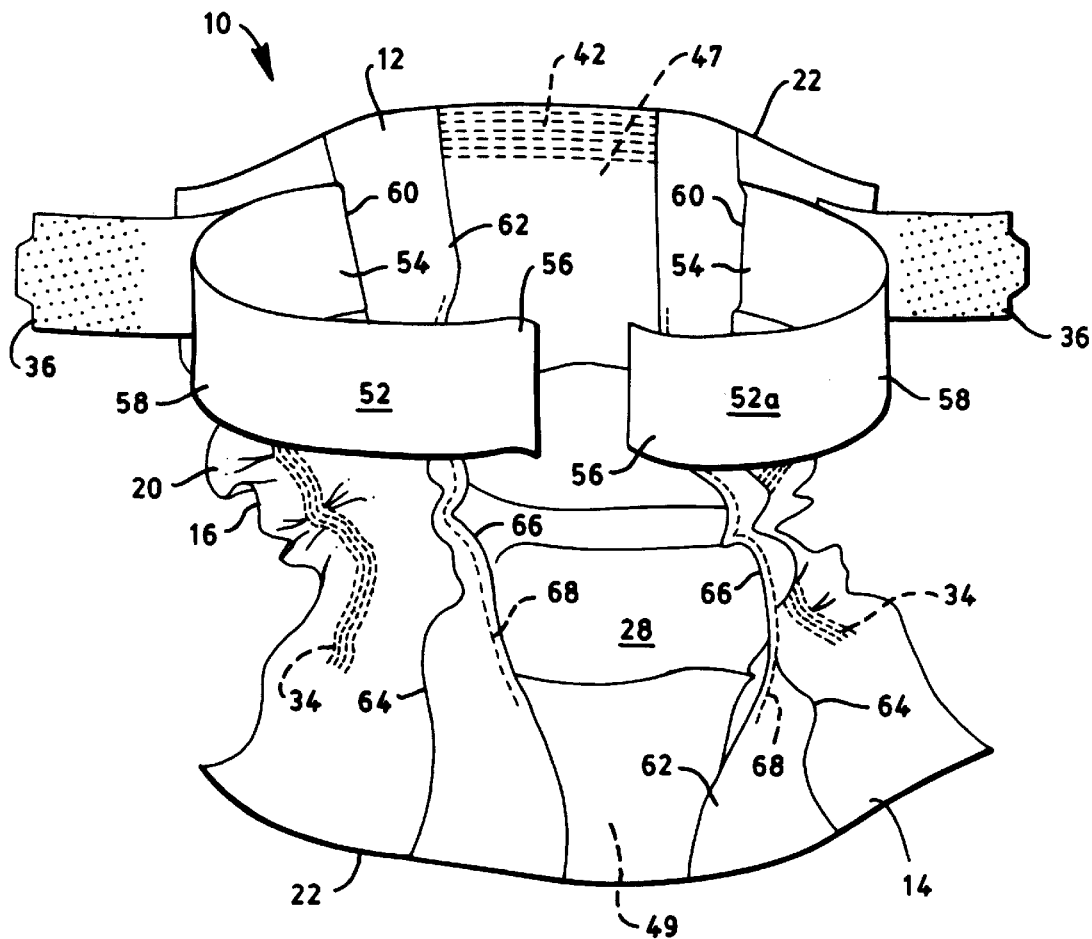
FIG. 11A representatively shows a perspective view of the article of FIG. 11 with its system of distribution belt components configured for placement about the wearer's waist and for placement in liquid communication with a front waistband section of the absorbent retention portion.
Figure 11B:
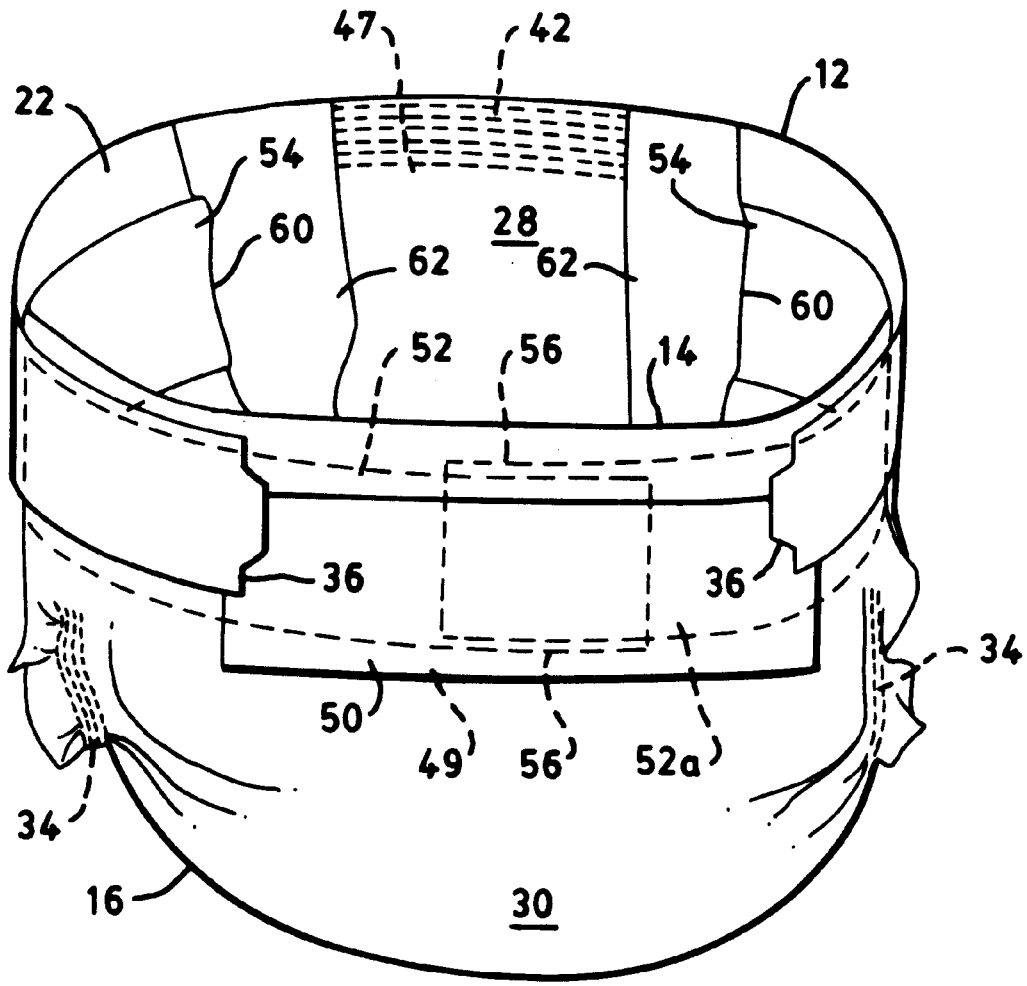
FIG. 11B representatively shows a perspective view of the article of FIG. 11 wherein its system of distribution belt components substantially surround the wearer's waist and overlap at the front waistband portion of the article for placement in liquid communication with the front waistband section of the absorbent retention portion, and wherein fasteners are configured to hold the article on the wearer.

With reference to FIGS. 11, 11A and 11B, the article of the invention can include first and second, laterally opposed distribution belt components 52 and 52a. The first belt component 52 can be appointed to extend along a first side of the wearer, such as the wearer's right-side, and the second belt component 52a can be appointed to extend along a second side of the wearer, such as the wearers left-side. Desirably, the belt components 52 and 52a are substantially the same, but may optionally be configured to differ from each other.

Each of the first and second belt components 52 and 52a has a lateral, transverse length sufficient to position the second end region 56 of each distribution belt component 52 and 52a in liquid communication with the second retention section 49 of the retention portion when the article is worn. In particular aspects of the invention, the first and second belt components 52 and 52a have a combined lateral, transverse length sufficient to substantially surround the wearer's waist area and contact each other at the second retention section 49 when the article is worn.

In the illustrated configuration, the first and second belt components 52 and 52a can be integrally formed with each other at the location of the first retention section 47. Alternatively, the first and second belt components 52 and 52a can be separately provided components which have their first end regions 54 joined to the article in liquid communication with the first retention section 47 of the article retention portion. In other arrangements, the first and second belt components 52 and 52a can be separately provided components that have their first end regions 54 assembled to each other at the appointed location of the retention portion 48. The assembled first end regions can be directly or indirectly attached to each other.

FIGS. 11 through 11A, representatively show the sequence of configuring the distribution belt components 52 and 52a during the placing and securing of the article on the wearer. In the shown arrangement, the diaper article includes both a right-side distribution belt component 52 and a complementary left-side distribution belt component 52a. Each distribution belt component has a first end region 54 which originates in the back waist portion of the absorbent and is brought into an operative contact with and secured to the front waistband portion of the absorbent retention portion 48 when the article is secured on the wearer. Desirably, each distribution belt component is brought into a substantially direct contact with the front waistband portion of the absorbent retention portion 48. In particular, the back waistband portion of the product is first placed underneath the lower back of the infant, and then the distribution belts are wrapped around the tummy of the infant so that the ends of the belts contact each other at the front waistband of the diaper. The front of the diaper was pulled up to completely cover the belts, and the fasteners are used to tightly close ears of the diaper around the infant's waist.

In alternative arrangements, each waist belt distribution component can originate from the front waist portion of the absorbent retention portion and be brought into an operative contact with and secured to the back waistband portion of the absorbent retention portion when the article is worn. Desirably, each distribution belt component is brought into a substantially direct contact with the back waistband portion of the absorbent retention portion 48.

Figure 12:
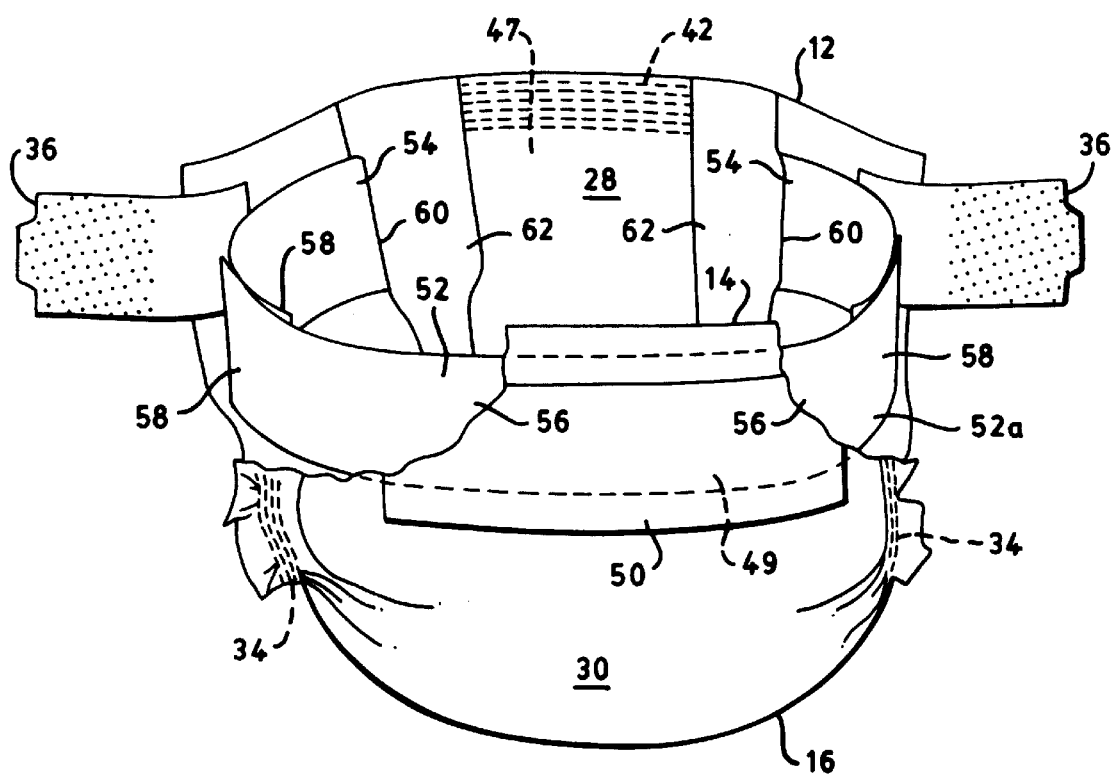
FIG. 12 representatively shows a partially cut-away, perspective view of an open article of the invention having a laterally opposed pair of distribution belt components in which the medial regions of the belt components are segments and are configured for placement in an overlapping arrangement when the article is worn.
Figure 12A:
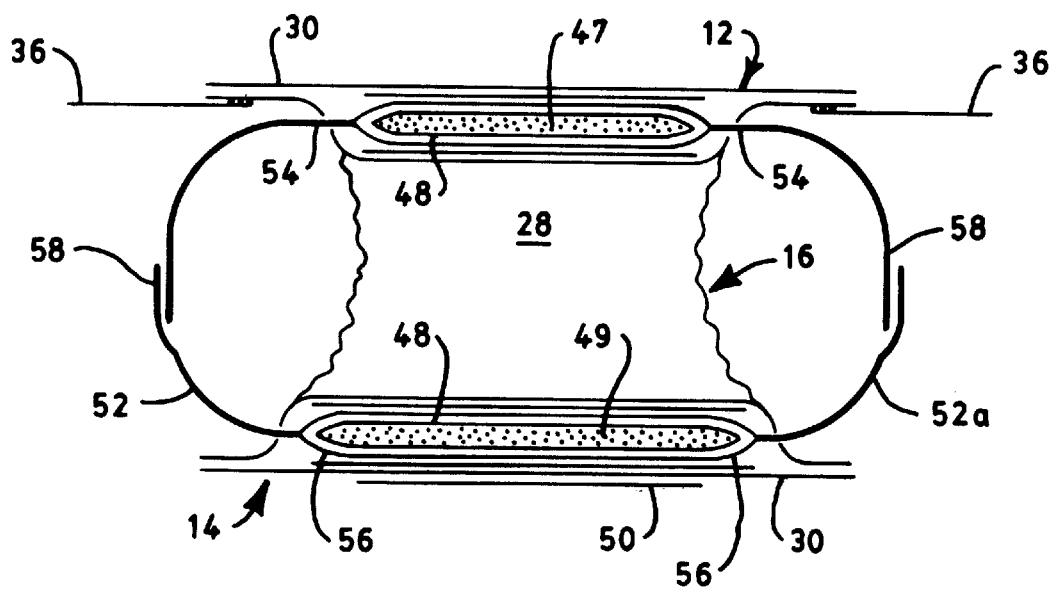
FIG. 12A representatively shows a schematic, expanded cross-sectional view of the article of FIG. 12 with its system of distribution belt components configured for placement about the wearer's waist and for placement in liquid communication with front and back waistband sections of the absorbent retention portion.

In typical arrangements of each distribution belt component 52, the belt first end region 54, the belt second end region 56 and the belt medial region 58 can be integrally formed as a single unit. Alternatively, each waist belt distribution component 52 can include a belt first end region 54 and a belt second end region 56 which are selectively interconnected by a belt medial region 58 which is segmented into a cooperating pair of split apart, separated sections, as representatively shown in FIGS. 12 and 12A. In the representatively shown arrangement, one of the end regions of each distribution belt component 52 and 52a can originate at each of the back and front waistband portions of the retention portion. In particular aspects of the invention, the belt first end region 54 can be attached in an operative liquid-communication with the first retention section 47, and the belt second end region 56 can be attached in an operative liquid-communication with the second retention section 49. The belt medial region 58 is configured to be joined together at an assembled medial region to thereby interconnect the belt first end region 54 and the belt second end region 56 along the sides of the wearer when the article is worn. The previously separated, distribution belt end regions can thereby be operably linked together to transport liquid from the region of high liquid saturation to the region of lower liquid saturation through the system of distribution belt components.

In still other configurations, the pair of belt components 52 can have the first end region, second end region and medial region of each belt component 52 integrally formed or otherwise joined with one another. Additionally, the first and second end regions can be operatively affixed to the first and second waistband portions of the article in liquid-communication with the corresponding first and second sections of the retention portion 48, The arrangements can be suitable for pants type articles, such as children's training pants. In further constructions, the first end regions of the two belt components 52 can be integrally formed or joined to each other, and in still further constructions, the second end regions of the two belt components may be integrally formed or joined to each other, as desired, to provide improved performance.

The following Examples are presented to provide a more detailed understanding of the invention, and are not intended to limit the scope of the invention.

EXAMPLE 1

A layered absorbent structure included an upper, bodyside layer and a lower, outward side layer. The upper absorbent layer was a 400 g/m$^2$ airlaid, homogeneous blend, composite composed of 20% Stockhausen W77553 superabsorbent polymer (an experimental superabsorbent obtained from Stockhausen, Inc., Greensboro, N. C. 75% HPF2 fiber (a mercerized southern softwood kraft pulp fiber obtained from Buckeye Absorbent Products), and 5% CELBOND T-255 binder fiber, which is an activated copolyolefin, bicomponent staple fiber obtained from Trevira (Hoechst Celanese), Salisbury, N. C. The upper layer also had a 0.2 g/cm$^3$ density.

The lower absorbent layer included two absorbent sheets composed of 100% Georgia Pacific High Heat Treated (GP HTT) fibers, which were microstrained fibers obtained from Georgia Pacific, Brunswick, Ga. Each absorbent sheet had a basis weight of 98 g/m$^2$ and a density of 0.116 g/cm$^3$. FAVOR 880 superabsorbent (obtained from Stockhausen, Inc.), at a basis weight of 225 g/m$^2$, was sandwiched and laminated between the two, absorbent sheets with sprays of H2525A adhesive, which is a rubber based hot melt adhesive obtained from Ato Findley, a business having offices in Wauwatosa, Wis.

Two distribution belt members were constructed from four, 98 g/m$^2$ sheets of GP HTT fibers. Each belt sheet had a length of 1.5 inches (3.8 cm) along the longitudinal direction 26, and a length of 17 inches (43.2 cm) along the lateral direction 24. Each belt member included two of the belt sheets lying side by side along the longitudinal direction. One belt member was attached to an outward facing surface of the lower absorbent layer and the other belt member was attached to the bodyside facing surface of the lower absorbent layer with adhesive sprays to form a composite distribution belt. The two belt members were arranged to sandwich the longitudinal end of the appointed back waistband portion of the lower absorbent layer, and side portions of the composite belt were arranged to extend transversely past the lateral side edges of the lower absorbent layer. Each side portion of the composite belt was composed of a two-layer laminate of the belt sheet material, and the belt side portions were symmetrically positioned on opposite sides of a longitudinally extending centerline of the absorbent structure. Accordingly, the configuration and assembly of the belt members into the article effectively provided a laterally opposed pair of belt components. The bodyside of the layered absorbent structure was covered with a bodyside tissue (e.g. the blue tissue described below) and the bodyside tissue was then covered with a liner or topsheet layer. The portions of the distribution belt which extended beyond the area of the layered absorbent structure were directed underneath the containment flaps of the final article and positioned on top of the liner or topsheet for wrapping around the wearer's waist during use.

To form a diaper article of this Example, the lower absorbent layer with the sheets of GP HTT material was cut into the pad shape representatively shown in FIG. 5A. The distribution belt members were attached to the back waistband end of the lower absorbent layer with fine sprays of H2525A adhesive. The upper absorbent layer was die cut into the shape representatively shown in FIG. 5, and the upper layer was placed on top of the lower layer with the shapes of the two layers registered to substantially match each other. The absorbent layers were wrapped in tissues. The tissue facing the upper layer was a blue tissue composed of Bleached Chemical Thermo-Mechanical Pulp (BCTMP) ligneous fibers formed by an UCTAD (UnCreped Through Air Dry process), and the tissue facing the lower layer was composed of a standard white forming tissue. The tissues were die cut to the desired, final absorbent shape. A 2.5 inch×6 inch (6.4 cm×15.2 cm), 2.5 osy (84.8 g/m$^2$) TABCW (through-air-bonded carded web) surge layer was attached along its longitudinally extending edges to the blue tissue side of the absorbent composite at a location approximately 2 inches (5.08 cm) away from the front edge of the lower layer absorbent using 0.25 inch (0.64 cm) wide, doublesided adhesive tape. The absorbent retention portion and surge layer were attached to a backsheet layer with a sprayed adhesive, and the topsheet layer was attached to the surge layer and the absorbent retention portion using very fine mists of adhesive. The topsheet material was excluded from the front waistband portion of the product to improve the conductivity of liquid between the retention portion and distribution belt members.

The test product of Example 1 was placed on a mannequin while the mannequin was in a prone position. The back waistband portion of the product was placed underneath the lower back of the mannequin, and the distribution belts were wrapped around the tummy of the mannequin so that the ends of the belts contacted each other at the front waistband of the diaper. The front of the diaper was pulled up to completely cover the belts, and fasteners were used to tightly close the ears of the diaper around the mannequin's waist.

Four separate additions of liquid (0.9% saline), measuring 80 ml for each addition, were introduced into the diaper, and the distributions of liquid were analyzed and measured. The results of the testing are summarized in the following TABLE 1.

TABLE 1

| Code | Fluid Held Back 5.5" (g) | Fluid Held Back Half (g) | Fluid Held Front Half (g) | Leakage at 4th Addition of liquid (g) |
| --- | --- | --- | --- | --- |
| Control | 87 | 133 | 184 | 2 |
| With Belt | 109 | 152 | 169 | 5 |

From the testing of Example 1, it can be seen that the belts can help increase absorbent utilization efficiency by transporting more liquid away from the front of the article to the back of the article, and by lowering the saturation in the front of the product where most of the liquid is initially introduced during use. As a result, the article can provide better fit (due to less sagging in the front), improved comfort and reduced leakage frequency (due to less saturation in the front of product).

EXAMPLE 2

A layered absorbent structure included an upper, bodyside layer and a lower, outward side layer. The upper absorbent layer was a 400 g/m² airlaid, homogeneous blend, composite composed of 20% Stockhausen W77553 superabsorbent polymer (an experimental superabsorbent obtained from Stockhausen, Inc., Greensboro, N. C., 75% HPF2 fiber (a mercerized southern softwood kraft pulp fiber obtained from Buckeye Absorbent Products), and 5% T-255 binder fiber (a bicomponent fiber obtained from Hoechst Celanese, Charlotte, N. C.). The upper layer also had a 0.2 g/cm³ density.

The lower absorbent layer included two absorbent sheets composed of 100% Georgia Pacific High Heat Treated (GP HTT) fibers (microstrained fibers obtained from Georgia Pacific, Brunswick, Ga.). Each absorbent sheet had a basis weight of 98 g/m² and a density of 0.116 g/cm³. FAVOR 880 superabsorbent (obtained from Stockhausen), at a basis weight of 80 g/m², was sandwiched and laminated between the two absorbent sheets with sprays of H2525A adhesive (a rubber based hot melt adhesive available from Ato Findley, Wauwatosa, Wis.).

A distribution belt was constructed from two, 98 g/m² sheets of GP HTT fibrous material. Each belt sheet had a length of 3 inches (7.6 cm) along the longitudinal direction 26, and a length of 17 inches (43.2 cm) along the lateral direction 24. One belt sheet was attached to the outward facing surface of the lower absorbent layer and the other belt sheet was attached to the bodyside surface of the lower absorbent layer with adhesive sprays to form a composite distribution belt. The two belt sheets were arranged to sandwich the longitudinal end of the appointed back waistband portion of the lower absorbent layer, and side portions of the distribution belt were arranged to extend transversely past the lateral side edges of the lower absorbent layer. Each side portion of the distribution belt was composed of a two layer laminate of the belt sheet material, and the belt side portions were symmetrically positioned on opposite sides of a longitudinally extending centerline of the absorbent structure. Accordingly, the configuration and assembly of the distribution belt into the article effectively provided a laterally opposed pair of belt components. The bodyside of the layered absorbent structure was covered with a bodyside tissue (e.g. the blue tissue described in Example 1) and the bodyside tissue was then covered with a liner or topsheet layer. The portions of the distribution belt which extended beyond the area of the layered absorbent structure were directed underneath the containment flaps of the final article and positioned on top of the liner or topsheet for wrapping around the wearer's waist during use.

A diaper of this Example was constructed and tested in manner similar to that employed for the construction and testing of the diaper of Example 1.

Figure 13:
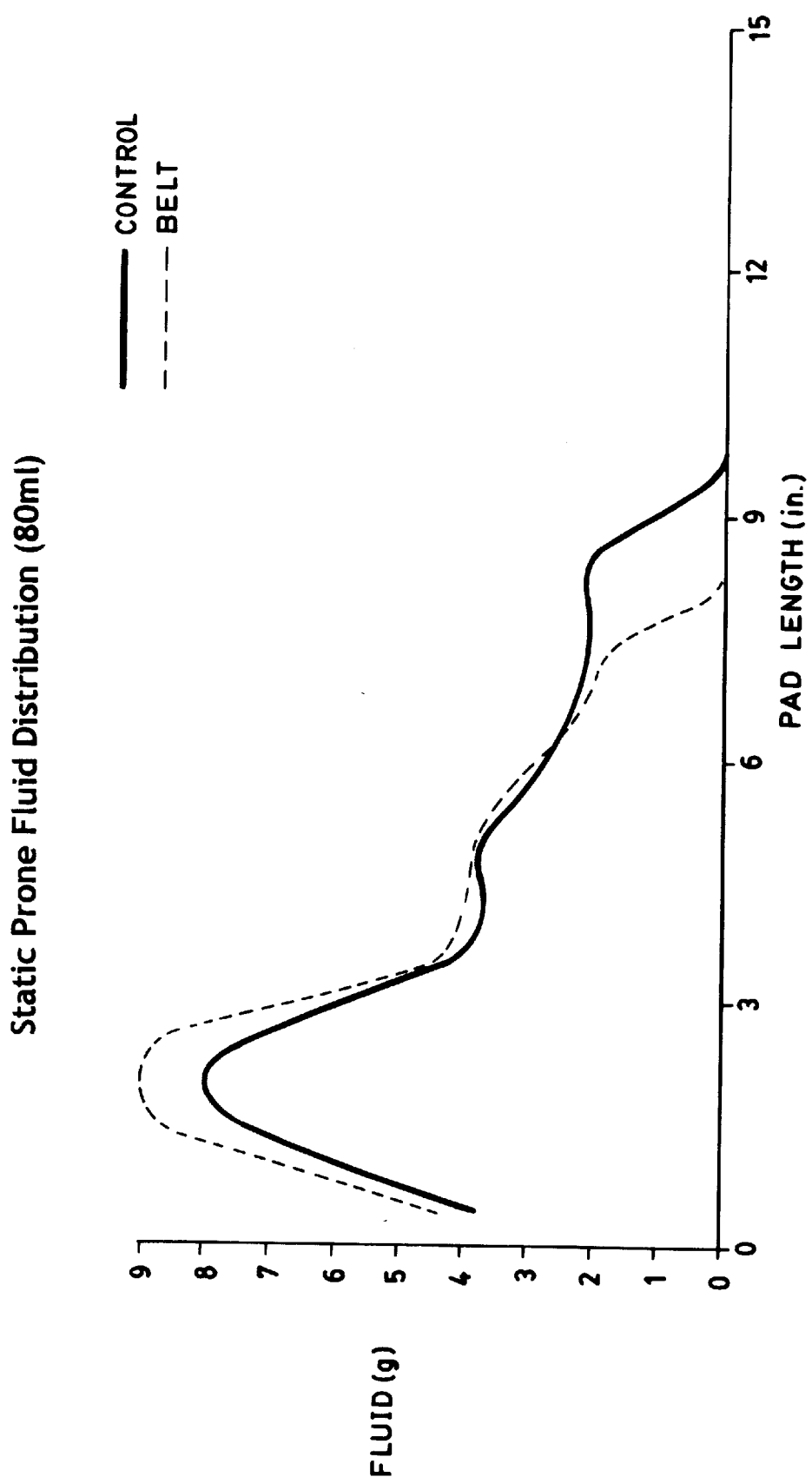
FIG. 13 is a graph which representatively shows the distribution of liquid in an article without a distribution belt and the distribution of liquid in an article with a distribution belt after a first quantity of liquid has been introduced into each article.
Figure 13A:
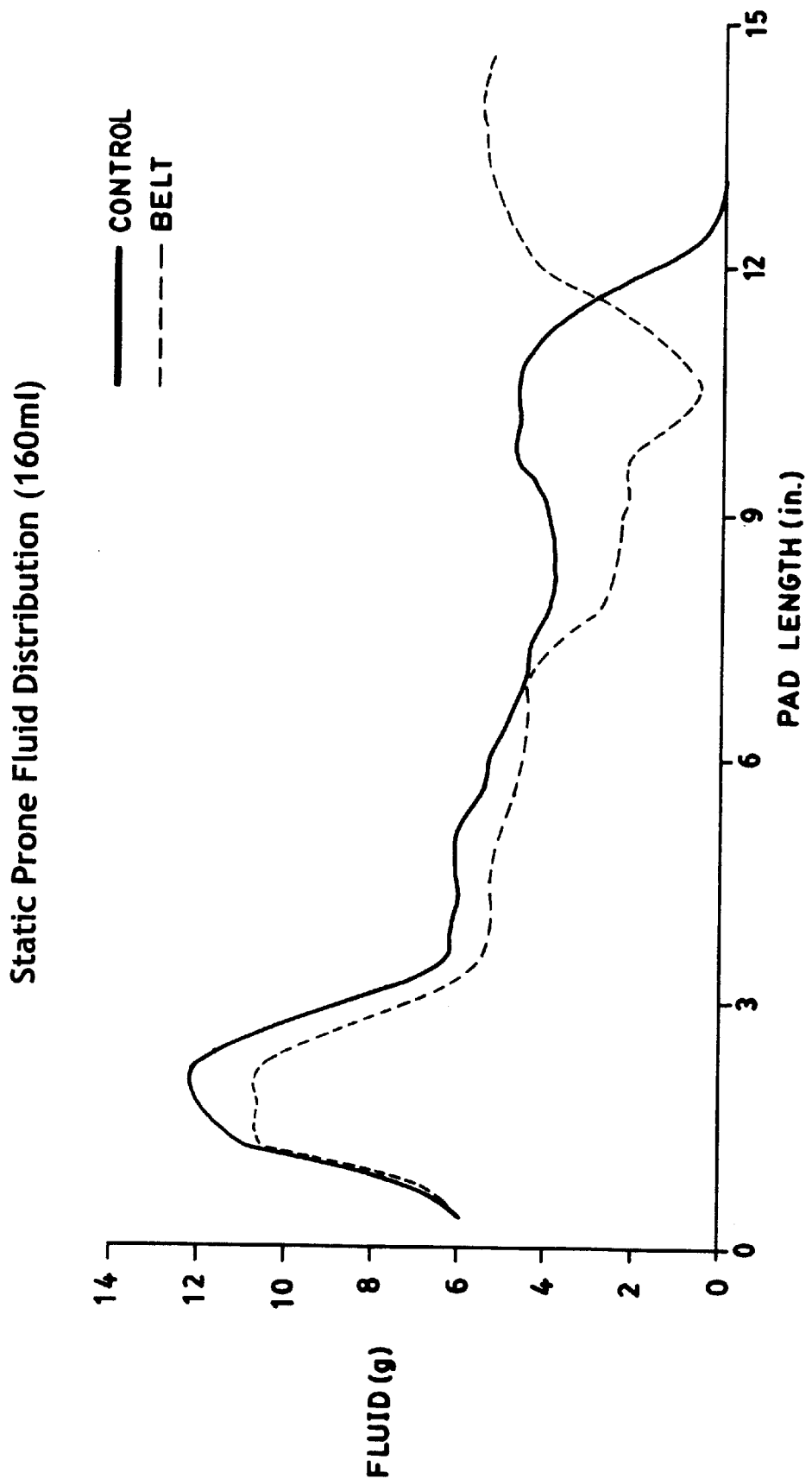
FIG. 13A is a graph which representatively shows the distribution of liquid in an article without a distribution belt and the distribution of liquid in an article with a distribution belt after a second quantity of liquid has been introduced into each article.
Figure 13B:
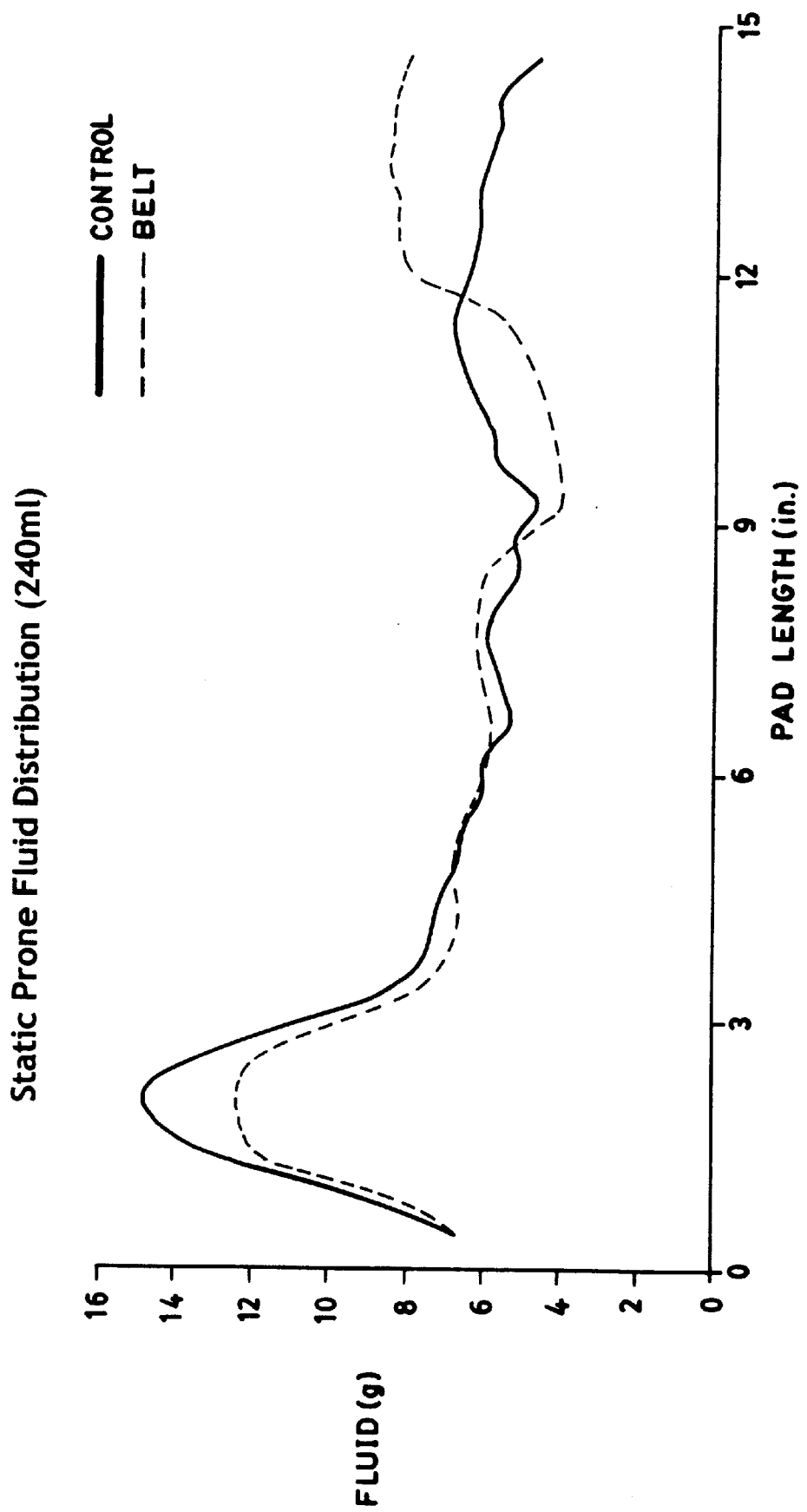
FIG. 13B is a graph which representatively shows the distribution of liquid in an article without a distribution belt and the distribution of liquid in an article with a distribution belt after a third quantity of liquid has been introduced into each article.

Three separate additions, measuring 80 ml of liquid in each addition, were introduced into the diaper, and the distributions of liquid were measured. The results of the testing are summarized in the following TABLE 2 and in the graphs of FIGS. 13, 13A and 13B.

TABLE 2

| Code | Fluid Held Back 5.5 inch (g) | Fluid Held Back Half (g) | Fluid Held Front Half (g) | Leakage (g) |
|---|---|---|---|---|
| 1st Addition of liquid | | | | |
| Control | 0.05 | 8.9 | 73.9 | 0 |
| With Belt | 0 | 2.0 | 81.6 | 0 |
| 2nd Addition of liquid | | | | |
| Control | 23.8 | 43.8 | 117.9 | 0 |
| With Belt | 42.5 | 55.7 | 104.8 | 0 |
| 3rd Addition of liquid | | | | |
| Control | 71.8 | 98.4 | 138.2 | 1.8 |
| With Belt | 81.2 | 108.4 | 131 | 0 |

From the testing of Example 2, it can be seen that the belts can provide improved benefits, particularly at loading of liquid that are greater than 80 ml. The belts can advantageously increase absorbent utilization efficiency by transporting more liquid away from the front of product to its back, and can lower the saturation in the front of the product where most of the liquid goes in during use. As a result, the absorbent article can provide better fit (due to less sagging in the front), improved comfort and reduced leakage frequency (due to less saturation in the front of product).

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a longitudinal direction, a lateral direction, a first waistband portion, a second waistband portion and an intermediate portion interconnecting said first and second waistband portions, said article comprising:
    a backsheet layer;
    a liquid permeable topsheet layer;
    an absorbent structure sandwiched between said backsheet and topsheet layers, said absorbent structure including a retention portion having a first retention section and a longitudinally opposed, second retention section; and
    a liquid distribution, waist belt component having a belt first end region, a belt second end region and a belt medial region which interconnects said belt first and second end regions when said article is worn, said belt first end region joined to said article in liquid communication with said first retention section, and said distribution belt component having sufficient lateral length to extend along a wearer's waist area to position said belt second end region in liquid communication with said second retention section when said article is worn.

2. An article as recited in claim 1 wherein, said belt first end region is joined in an indirect contact with said first retention section.

3. An article as recited in claim 1 wherein, said belt first end region is joined in a substantially direct contact with said first retention section.

4. An article as recited in claim 1 wherein, said belt first end region, said belt second end region and said belt medial region are integrally formed as a single unit.

5. An article as recited in claim 1 wherein, said belt first end region is attached to said first retention section, said belt second end region is attached to said second retention section, and said belt medial region is configured to be assembled to interconnect said belt first end region and said belt second end region when said article is worn.

6. An article as recited in claim 1 wherein, said belt first end region extends through an aperture in a first waistband portion of said topsheet layer.

7. An article as recited in claim 1 wherein, said topsheet layer is configured to provide an indirect contact between said belt second end region and said second retention section.

8. An article as recited in claim 1 wherein, said topsheet layer is configured to provide a substantially direct contact between said belt second end region and said second retention section.

9. An article as recited in claim 1 wherein, said topsheet layer includes at least one cooperating aperture in a second waistband portion of said topsheet layer to provide said substantially direct contact between said belt second end region and said second retention section.

10. An article as recited in claim 1 wherein, said belt second end region has a curved shape.

11. An article as recited in claim 1 wherein, said article further comprises a laterally opposed pair of fasteners which, when said article is worn, are positioned outward of said distribution belt and secure said article on said wearer.

12. An article as recited in claim 1 wherein, said distribution belt component can provide a Liquid Flux value of at least about 0.002 gm/min/gsm/in.

13. An article as recited in claim 1 wherein, said distribution belt component is composed of a wettable material with a basis weight of at least a minimum of about 50 g/m$^2$.

14. An article as recited in claim 1 wherein, said distribution belt component is composed of a wettable material with a density of at least a minimum of about 0.1 g/cm$^3$.

15. An article as recited in claim 1 wherein, said first retention section is located in an appointed back waistband portion of said article.

16. An article as recited in claim 1 wherein, said first retention section is located in an appointed front waistband portion of said article.

17. An article as recited in claim 1 wherein, said distribution belt component includes a first belt layer and at least a second belt layer.

18. An article as recited in claim 1 wherein, said distribution belt component includes a first belt layer and at least a second belt layer, said first and second belt layers configured to sandwich a least a portion of said first retention section.

19. An article as recited in claim 1 wherein, said retention portion includes a first retention layer and at least a second retention layer, and at least a portion of said distribution belt component is interposed between said first and second retention layers.

20. An article as recited in claim 1 wherein, said retention portion includes a first retention layer and at least a second retention layer, said distribution belt component includes a first belt layer and at least a second belt layer, and at least a portion of said first belt layer is interposed between said first and second retention layers.

21. An article as recited in claim 20, wherein at least a portion of said second belt layer is substantially adjacent said second retention layer and interposed between said second retention layer and said backsheet layer.

22. An article as recited in claim 20, wherein said first belt layer is located on a bodyside surface of said second belt layer and configured to be interposed between said second belt layer and said wearer when the article is worn.

23. An article as recited in claim 20 wherein, said first belt layer is located on a bodyside surface of said second belt layer and configured to contact said wearer when the article is worn.

24. An article as recited in claim 1 wherein, said article includes first and second, laterally opposed distribution belt components, said first belt component appointed to extend along a first side of said wearer, and said second belt component appointed to extend along a second side of said wearer.

25. An article as recited in claim 24 wherein, said first and second belt components have a combined lateral length sufficient to surround said wearer's waist area and contact each other at said second retention section when the article is worn.

26. An article as recited in claim 24 wherein, said first and second belt components are attached to each other at said first retention section.

27. An article as recited in claim 24 wherein, said first and second belt components are integrally formed with each other at said first retention section.

* * * * *

UNITED STATES PATENT AND TRADEMARK OFFICE
CERTIFICATE OF CORRECTION

PATENT NO.   : 6,245,051 B1
DATED        : June 12, 2001
INVENTOR(S)  : David Louis Zenker, Hoa La Wilhelm and Rob David Everett It is certified that error appears in the above-identified patent and that said Letters Patent is hereby corrected as shown below:

Column 3,
Line 45, delete "With" and substitute -- with --.

Column 7,
Line 54, delete "worm" and substitute -- worn --.

Column 11,
Line 16, delete "is".

Column 12,
Line 36, delete "Altematively" and substitute -- Alternatively --.

Column 13,
Line 25, delete "Altematively" and substitute -- Alternatively --.

Column 17,
Line 12, delete "issue" and substitute -- tissue --.

Column 19,
Line 4, "9/cm$^3$" and substitute -- g/cm$^3$ --.

Column 23,
Line 66, insert -- . -- after "waist".

Column 25,
Line 12, insert -- . -- after "structure".
Line 12, delete "Altematively" and substitute -- Alternatively --.

UNITED STATES PATENT AND TRADEMARK OFFICE
CERTIFICATE OF CORRECTION

PATENT NO.   : 6,245,051 B1
DATED        : June 12, 2001
INVENTOR(S)  : David Louis Zenker, Hoa La Wilhelm and Rob David Everett It is certified that error appears in the above-identified patent and that said Letters Patent is hereby corrected as shown below:

<u>Column 27,</u>
Line 63, delete "disdosures" and substitute -- disclosures --.

<u>Column 31,</u>
Line 12, delete "worm" and substitute -- worn --.
Line 25, delete "Altematively" and substitute -- Alternatively --.

Signed and Sealed this

Twelfth Day of November, 2002

*Attest:*

*Attesting Officer*

JAMES E. ROGAN
*Director of the United States Patent and Trademark Office*